(12) United States Patent
Majumdar et al.

(10) Patent No.: US 10,471,101 B2
(45) Date of Patent: Nov. 12, 2019

(54) MANAGEMENT OF ISCHEMIA USING POOLED MESENCHYMAL STROMAL CELL COMPOSITION

(71) Applicant: STEMPEUTICS RESEARCH PVT. LTD., Bangalore (IN)

(72) Inventors: Anish Sen Majumdar, Bangalore (IN); Pawan Kumar Gupta, Bangalore (IN); Anoop Chullikana House, Bangalore (IN); Sudha Balasubramanian, Bangalore (IN); Charan Thej, Bangalore (IN); Mathiyazhagan Rengasamy, Bangalore (IN)

(73) Assignee: Stempeutics Research PVT. LTD., Bangalore (IN)

( * ) Notice: Subject to any disclaimer, the term of this patent is extended or adjusted under 35 U.S.C. 154(b) by 0 days.

(21) Appl. No.: 15/128,942

(22) PCT Filed: Mar. 25, 2015

(86) PCT No.: PCT/IB2015/052197
§ 371 (c)(1),
(2) Date: Sep. 23, 2016

(87) PCT Pub. No.: WO2015/145370
PCT Pub. Date: Oct. 1, 2015

(65) Prior Publication Data
US 2017/0100434 A1 Apr. 13, 2017

(30) Foreign Application Priority Data

Mar. 26, 2014 (IN) .............................. 1620/CHE/2014

(51) Int. Cl.
*A61K 35/28* (2015.01)
*C12N 5/077* (2010.01)
*C12N 5/0775* (2010.01)

(52) U.S. Cl.
CPC ............ *A61K 35/28* (2013.01); *C12N 5/0663* (2013.01); *C12N 5/0669* (2013.01); *C12N 2502/1394* (2013.01)

(58) Field of Classification Search
CPC .... A61K 35/28; C12N 5/0669; C12N 5/0663; C12N 2502/1394
See application file for complete search history.

(56) References Cited

FOREIGN PATENT DOCUMENTS

WO 2011064733 A1 6/2011
WO 2012131618 A1 10/2012

OTHER PUBLICATIONS

Liew et al. Therapeutic potential for mesenchymal stem cell transplantation in critical limb ischemia. Stem Cell Research & Therapy 2012, 3:28; p. 1-14 (Year: 2012).*
Suzuki et al. Clinical Application of Vascular Regenerative Therapy for Peripheral Artery Disease. BioMed Research International vol. 2013, Article ID 179730, p. 1-6 (Year: 2013).*
Wang et al. Mesenchymal stem cell-conditioned medium facilitates angiogenesis and fracture healing in diabetic rats. J Tissue Eng Regen Med 2012;6: 559-569 (Year: 2012).*
"Stempeutics announces clinical trial outcome of India's First stem cell product Stempeucel," Stempeutics Press Release, Available Online at http://www.stempeutics.com/pdf/article_1.pdf, Apr. 27, 2010, 2 pages.
Das, A. et al., "Intra-arterial Allogenic Mesenchymal Stem Cells for Critical Limb Ischemia are Safe and Efficacious: Report of a Phase I Study," World Journal of Surgery, vol. 37, No. 4, Apr. 2013. Published Online Jan. 10, 2013, 8 pages.
Gupta, P. et al., "A double blind randomized placebo controlled phase I/II study assessing the safety and efficacy of allogeneic bone marrow derived mesenchymal stem cell in critical limb ischemia," Journal of Translational Medicine, vol. 11, No. 143, Jun. 10, 2013, 11 pages.
"Stempeutics Research Pvt Ltd, Stem Cell Research and Product Development, Stem Cells, Clinical Trials: Stempeucel," Available Online at http://web.archive.org/web/20140109202206/http://www.stempeutics.com/stempeucel.html, Available as Early as Jan. 9, 2014, 2 pages.
Chullikana, A. et al., "Randomized, double-blind, phase I/II study of intravenous allogeneic mesenchymal stromal cells in acute myocardial infarction," Cytotherapy, vol. 17, No. 3, Mar. 2015, Published Online Dec. 4, 2014, 12 pages.
ISA European Patent Office, International Search Report and Written Opinion Issued in Application No. PCT/IB2015/052197, dated May 28, 2015, WIPO, 12 pages.

* cited by examiner

*Primary Examiner* — Taeyoon Kim
(74) *Attorney, Agent, or Firm* — McCoy Russell LLP

(57) ABSTRACT

The present disclosure relates to composition comprising pooled and expanded allogeneic mesenchymal Stromal cells (MSCs) and a method for management of Ischemia using the composition thereof. In particular, the disclosure relates to bone marrow derived pooled and expanded allogeneic MSC compositions with effective dosage ranges and modes/route of administration for effective management of Ischemia. The disclosure also relates to the use of conditioned medium rich in bioactive factors in combination with the cell composition for managing ischemic conditions.

16 Claims, 19 Drawing Sheets

MANAGEMENT OF ISCHEMIA USING POOLED MESENCHYMAL STROMAL CELL COMPOSITION

CROSS REFERENCE TO RELATED APPLICATIONS

The present application is a U.S. National Phase of International Patent Application No. PCT/IB2015/052197, entitled "MANAGEMENT OF ISCHEMIA USING POOLED MESENCHYMAL STROMAL CELL COMPOSITION", filed on Mar. 25, 2015, which claims priority to Indian Patent Application No. 1620/CHE/2014, entitled "MANAGEMENT OF ISCHEMIA USING POOLED MESENCHYMAL STROMAL CELL COMPOSITION", filed on Mar. 26, 2014, the entire contents of each of which are hereby incorporated by reference for all purposes.

TECHNICAL FIELD

The present disclosure relates to the field of stem cell therapy. In particular, the disclosure relates to compositions comprising pooled allogeneic mesenchymal Stromal cells (MSCs) for management of ischemic conditions.

BACKGROUND OF THE DISCLOSURE

Buerger's disease (also known as Thromboangiitis obliterans) is a recurring progressive inflammation and thrombosis (clotting) of small and medium arteries and veins of the hands and feet. One of the most common conditions arising due to Buerger's disease is Critical Limb Ischemia (CLI) that might result in amputation and limb loss.

CLI, an ischemic condition, is also a symptom of Peripheral Arterial Disease (PAD). Peripheral artery disease (PAD), also known as peripheral vascular disease (PVD) peripheral artery occlusive disease, and peripheral obliterative arteriopathy, is a condition resulting due to narrowing of arteries other than those that supply the heart or brain. Most commonly the legs and feet are affected. The classic symptom is leg pain when walking which resolves with rest. Other symptoms including: skin ulcers, bluish skin, cold skin, or poor nail and hair growth may occur in the affected leg. Complications may include an infection or tissue death which may lead to amputation, coronary artery disease, or stroke.

Symptoms of PAD in the legs and feet are generally divided into 2 categories:
Claudication—pain in muscles when walking or using the affected muscles that is relieved by resting those muscles. This is due to the unmet oxygen demand in muscles with use in the setting of inadequate blood flow; and
Critical limb ischemia, consisting of:
Rest pain, a pain in the soles of the feet, particularly when the feet are elevated, such as when in bed.
Tissue loss, consisting of arterial insufficiency ulcers, which are sores or wounds that heal slowly or not at all, and Gangrene.

Incidence of critical limb ischemia is estimated to be approximately 500 to 1000 patients per million per year. CLI includes all patients with chronic ischemic rest pain, ulcers or gangrene attributable to objectively proven arterial occlusive disease. CLI arises as a result of atherosclerosis or vasculitis in leg arteries which severely impairs the patient functional status and quality of life and is associated with an increased cardiovascular mortality and morbidity. The annual overall major cardiovascular event rate [non-fatal myocardial infarction (MI), stroke and vascular death] in peripheral artery disease (PAD) patients is around 4-7%.

Narrowed vessels that cannot supply sufficient blood flow to exercising leg muscles may cause claudication, which is brought on by exercise and relieved by rest. As vessel narrowing increases, CLI can develop when the blood flow does not meet the metabolic demands of tissue at rest. 10% to 40% of the patients are at the risk of primary amputation.

Patients with CLI generally have a one and ten year mortality rates of approximately 20% and 75% respectively. Current mode of treatment has failed to show significant improvements in these "no-option" patients of CLI. Gradually the disease progresses resulting in gangrene and subsequently amputation of the affected limb at younger age. Prognosis of CLI is poor and no effective treatments have been established in patients who are not amenable for the traditional revascularization therapies ("no—option" patients) such as angioplasty and bypass procedures due to the inappropriate anatomy of the leg arteries or frequent re-occlusion following revascularization. Studies have shown that the amputation rate varies from 40% to 70% in these groups of patients with the standard protocol of care. Therefore, it is necessary to establish new revascularization treatments to improve prognosis of these patients.

Ischemic cardiomyopathy (ICM) is another ischemic condition which is the leading cause of cardiac failure worldwide. It leads to a great loss of productive years of life in people aged 40 and above. Chronic ischemia leads to myocardial cell death and ultimately loss of the myocardium, which in turn causes clinical heart failure and other dire consequences of arrhythmias and sudden cardiac death. Despite significant advances in medical therapy and interventional strategies, the prognosis of millions of patients with ischemic cardiomyopathy (ICM) and cardiac failure remains dismal.

The present disclosure aims to overcome the drawbacks observed in the currently available treatments for ischemic conditions by providing efficient Stromal cell therapy.

Statement of Disclosure

The present disclosure relates to a composition for managing ischemia comprising pooled and expanded allogeneic mesenchymal stromal cells in an amount ranging from about 1 million cells to 1000 million cells, optionally along with pharmaceutically acceptable excipient; a method of managing ischemia in a subject having or suspected of having the ischemia, said method comprising acts of administering a composition comprising pooled and expanded allogeneic mesenchymal stromal cells at a dose ranging from about 0.5 million cells per kg of body weight of the subject to 5 million cells per kg of body weight of the subject, optionally along with pharmaceutically acceptable excipient to the subject; a kit for treating ischemia in a subject in need thereof comprising the composition optionally along with: (a) a conditioned medium derived from pooled allogeneic mesenchymal stromal cells wherein said conditioned medium comprises bioactive factors selected from a group comprising VEGF, Ang1, and TGF β, or any combination thereof, or (b) an instruction manual, or a combination of (a) and (b) thereof; a composition comprising pooled and expanded allogeneic mesenchymal stromal cells in an amount ranging from about 1 million cells to about 1000 million cells, optionally along with pharmaceutically acceptable excipient for use as a medicament.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure where:

Figure 14:
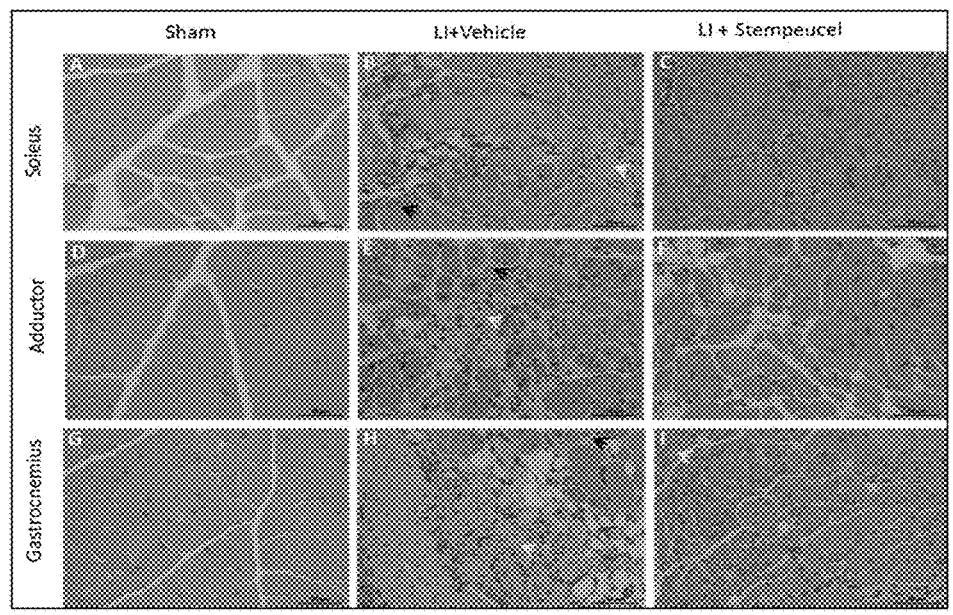

FIG. 14 depicts the muscle histology (H&E) of sham, LI+vehicle and LI+Stempeucel® treated animals after 28 days. A (soleus), D (adductor) and G (gastrocnemius) represents the cross sections of skeletal muscles of sham animals showing the normal histology of muscle fibers with a peripheral nucleus arranged in muscle bundles with occasional blood vessels seen in between. B (Soleus), E (Adductor) and H (Gastrocnemius) represents the cross sections of the skeletal muscles of LI treated with vehicle group showing severe vacuolar degeneration (Red arrow), infiltration of inflammatory cells (Green arrow), necrosis of muscle fibres (Yellow arrow), Degeneration of muscle fibres (Blue arrow) and atrophy of muscle fibres (Black arrow). C (Soleus), I (Adductor) and F (Gastrocnemius) represents the cross sections of the skeletal muscles of LI animals treated with Stempeucel® show very mild degeneration of muscle fibers (Blue arrow), infiltration of inflammatory cells (Green arrow) and necrosis of muscle fibers (Yellow arrow). Many regenerating muscle fibres (red arrow) with a centrally placed nucleus are observed. Photographs were taken at 40× magnification and Scale bar shows the 50 µm.

Figure 15:
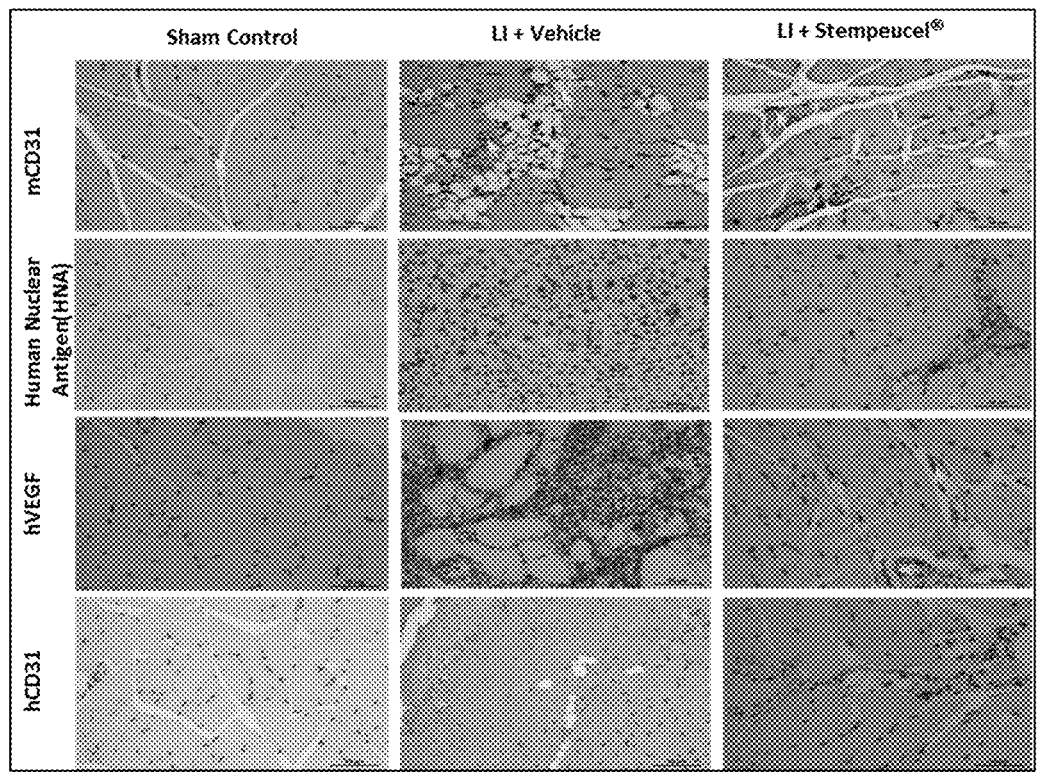

FIG. 15 depicts the immunohistochemistry images of Stempeucel® treatment in mouse hind limb ischemic muscles: Adductor Muscle tissues of limb ischemia of sham, LI+Vehicle, LI+Stempeucel® animals after 28 days were immunostained with Human CD31, Mouse CD31, human VEGF and Human HNA. All measurements were performed in a blinded manner. Five different fields were randomly studied for each mouse and viewed at 40× viewing fields for positive immunoactivity. Photographs were taken at 40× magnification and Scale bar shows the 50 µm.

Figure 16:
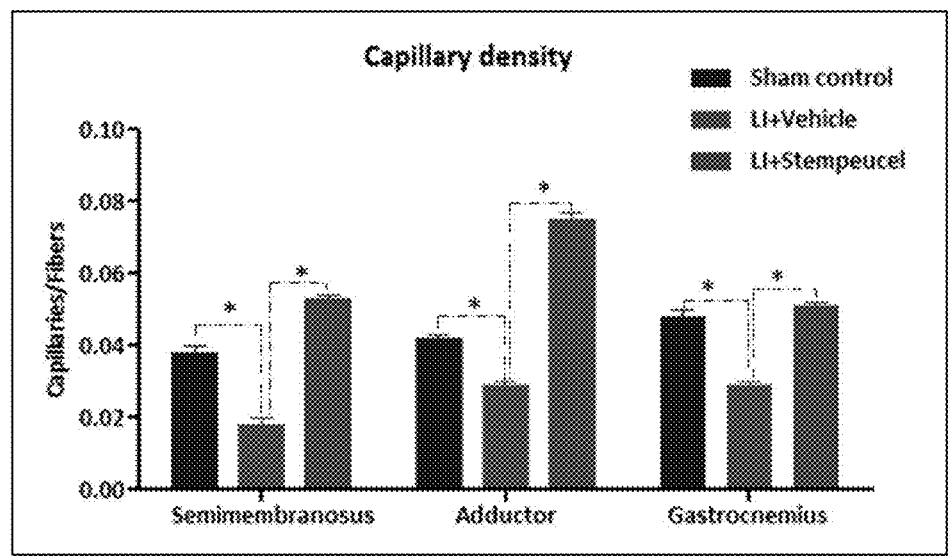

FIG. 16 depicts the capillary density of sham, LI+Vehicle and LI+Stempeucel® animals at 28 day after LI. Values are expressed as Mean±SEM., #$p<0.05$ Sham control Vs LI vehicle; *$p<0.05$ LI+Vehicle Vs LI+Stempeucel®.

Figure 17A:
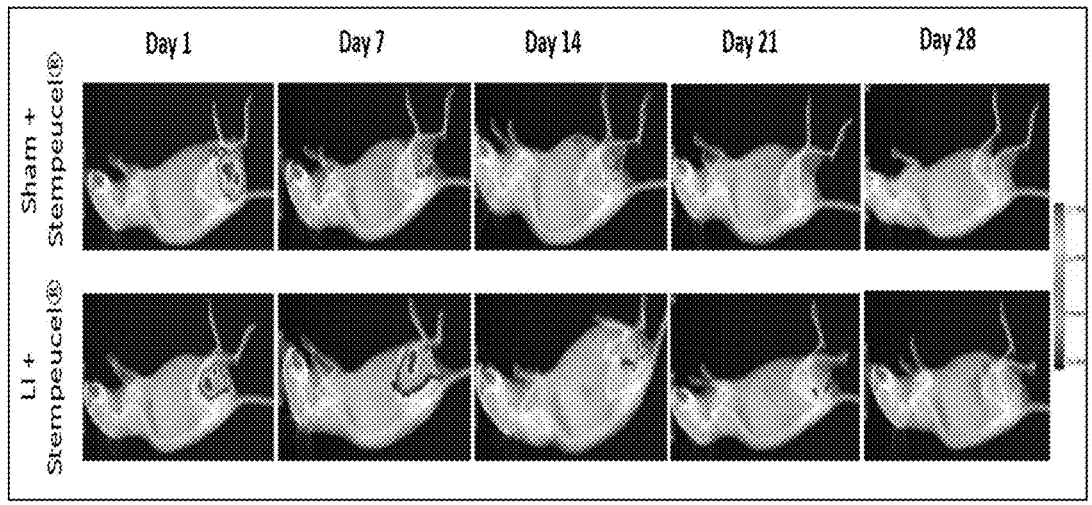

FIG. 17A depicts in vivo imaging of sham and LI animals treated with Stempeucel®.

Figure 17B:
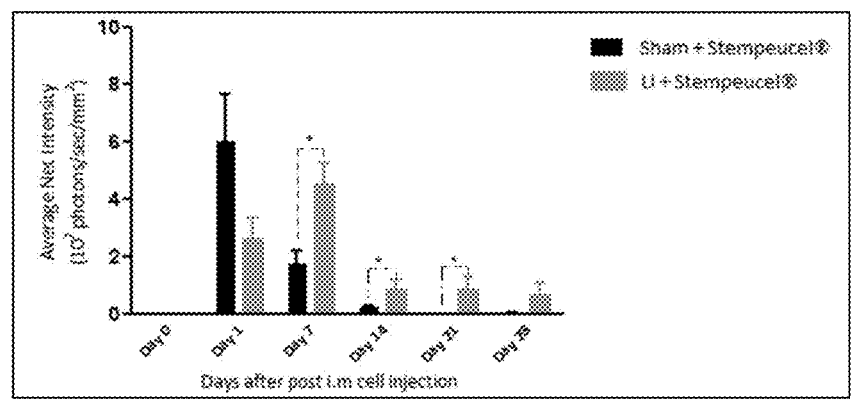

FIG. 17B depicts Bio-distribution intensity analysis of sham and LI animals treated with Stempeucel® at different time points. Values are expressed as mean ±SEM. *$p<0.05$.

Figure 18:
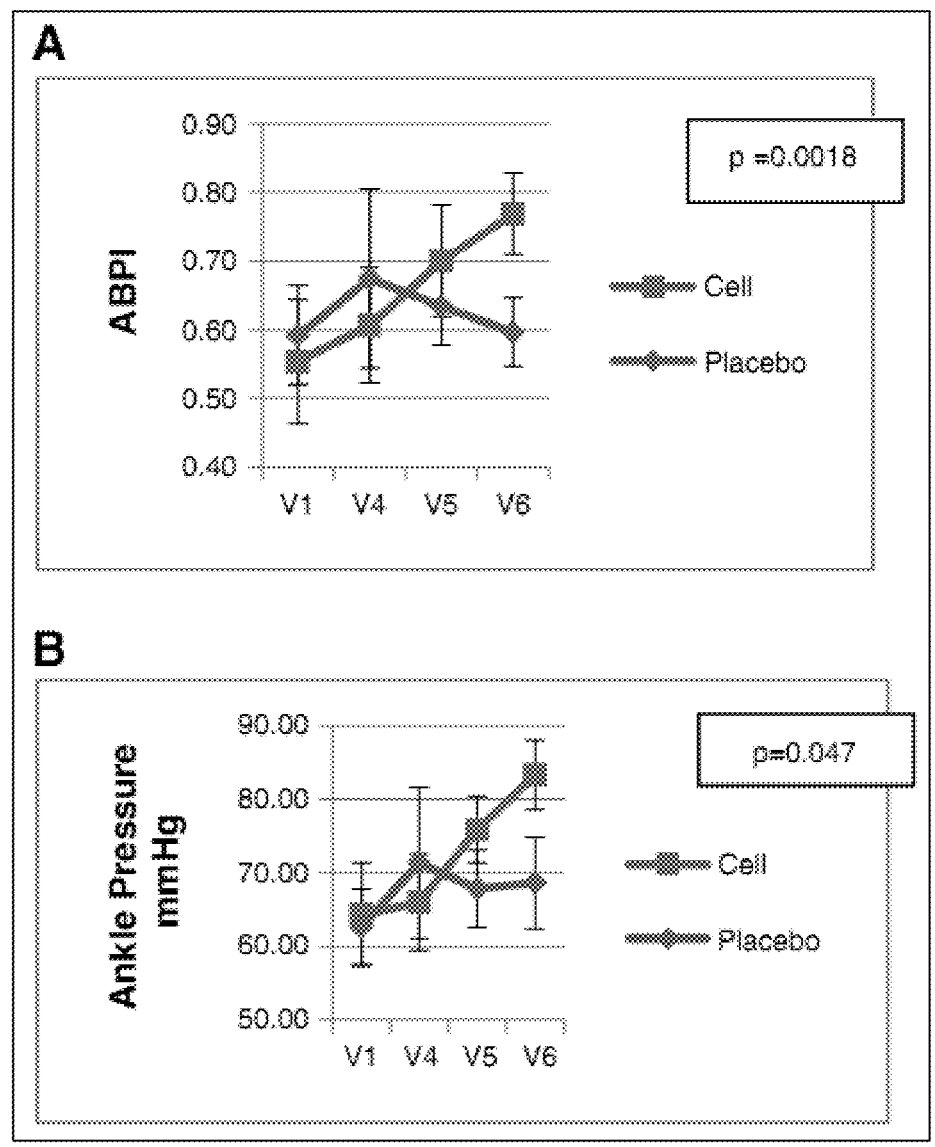

FIG. 18 depicts the results of efficacy parameters in CLI subjects following intramuscular (IM) injection of allogeneic BM-MSCs (cell) and placebo. Results of ABPI (A) & Ankle pressures (B) are shown as mean±SD and corresponding 'p' values. V1: screening; V4: 1 month; V5: 3 month; V6: 6 month follow-ups.

Figure 19:
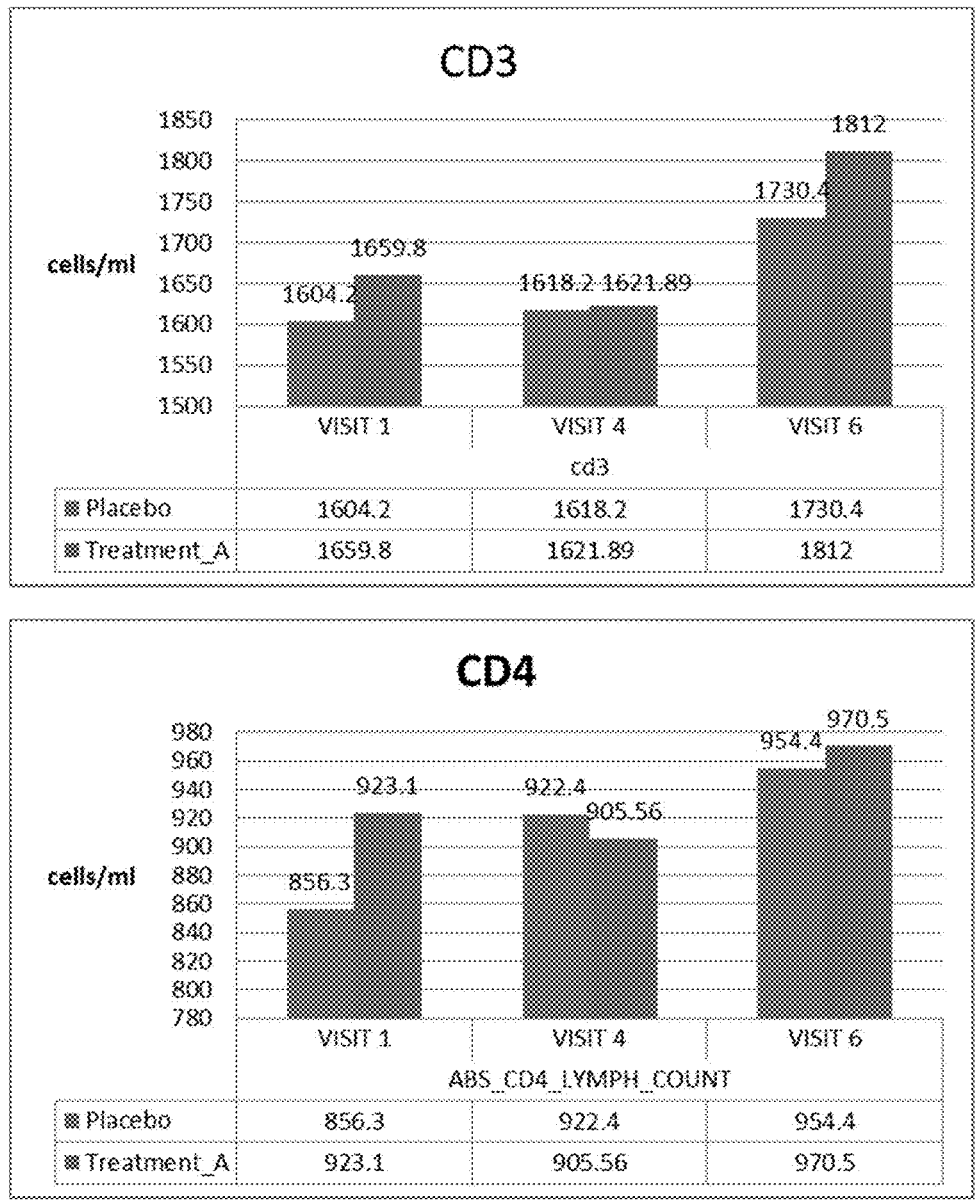

FIG. 19 depicts the graphical representation of Mean Change from Baseline in Mean CD3 and CD4 counts Immunological parameters per visit.

Figure 20:
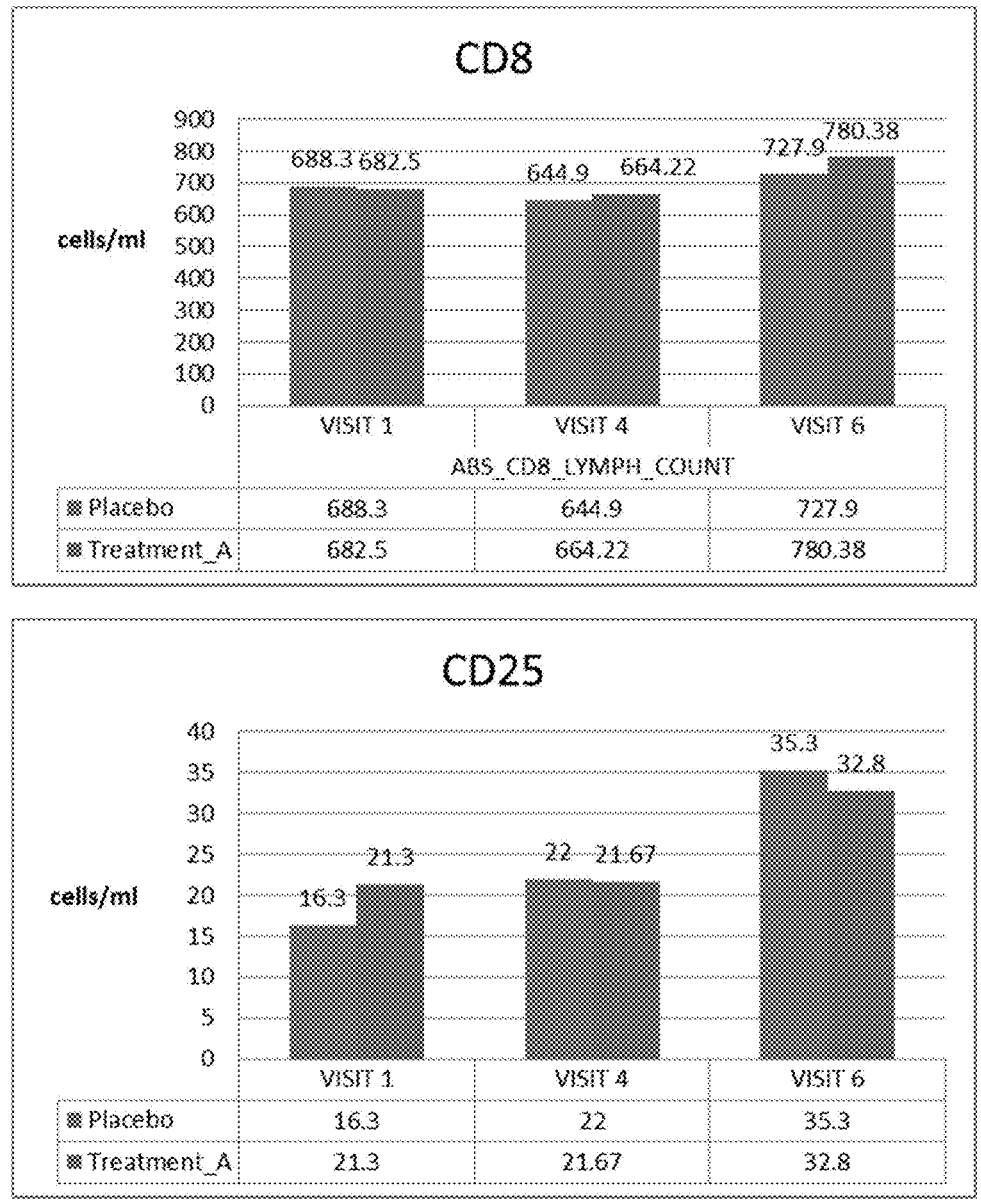

FIG. 20 depicts the graphical representation of Mean Change from Baseline in Mean CD8 and CD25 counts Immunological parameters per visit.

Figure 21:
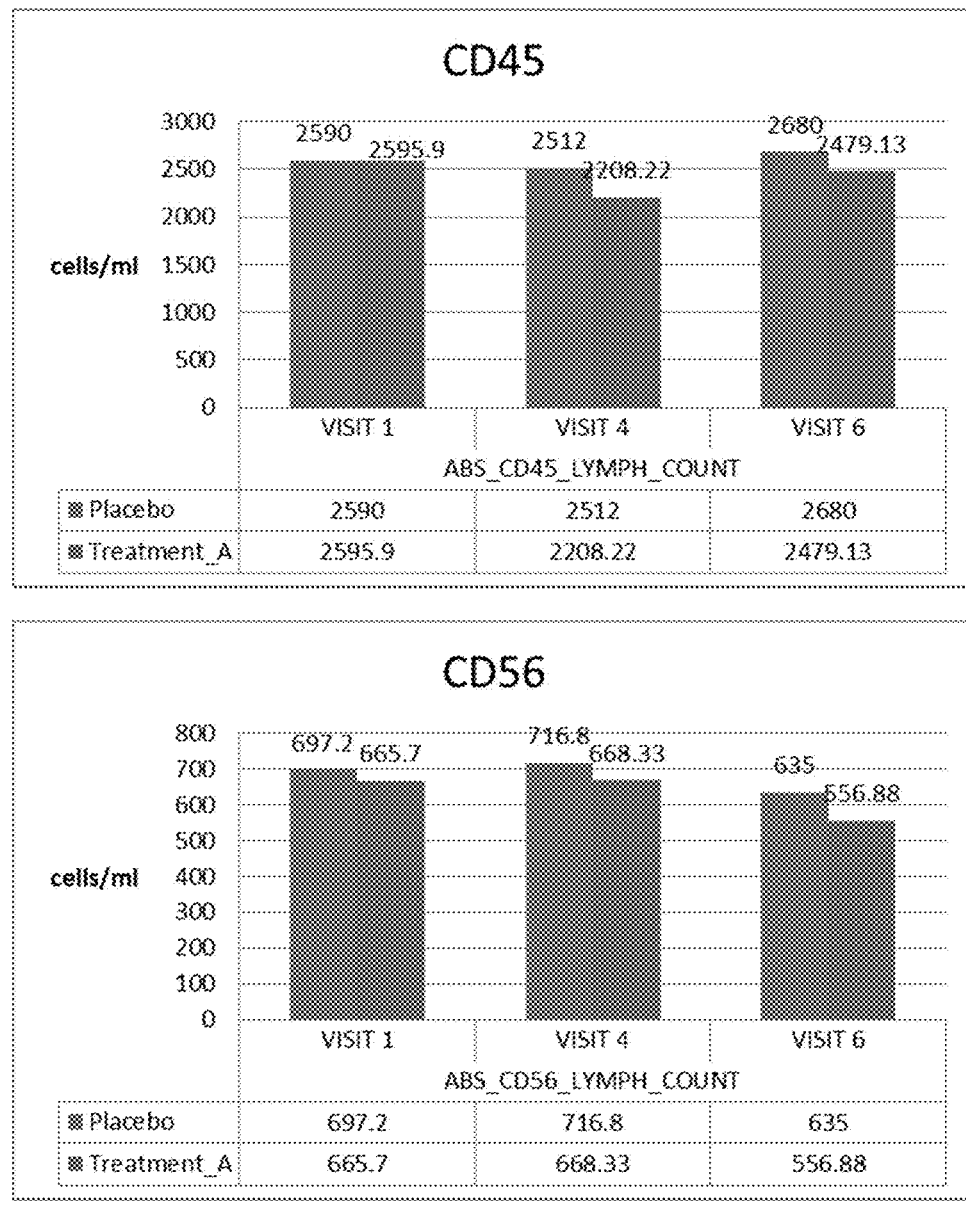

FIG. 21 depicts the graphical representation of Mean Change from Baseline in Immunological parameters Mean CD45 and CD56 counts per visit.

Figure 22:
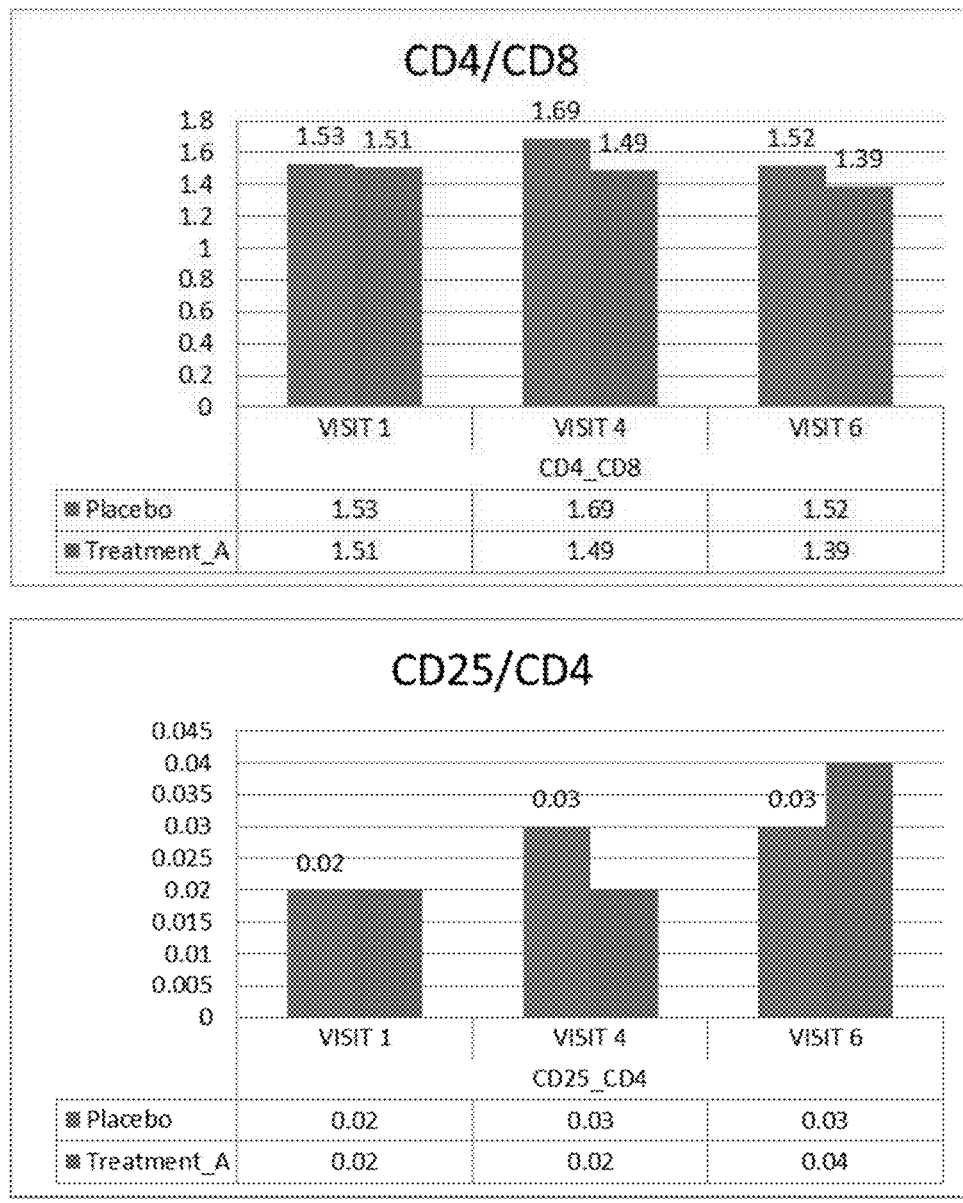

FIG. 22 depicts the graphical representation of Mean Change from Baseline in Immunological parameters Mean CD4/CD8 ratio and CD25/CD4 per visit. are depicted.

Figure 23:
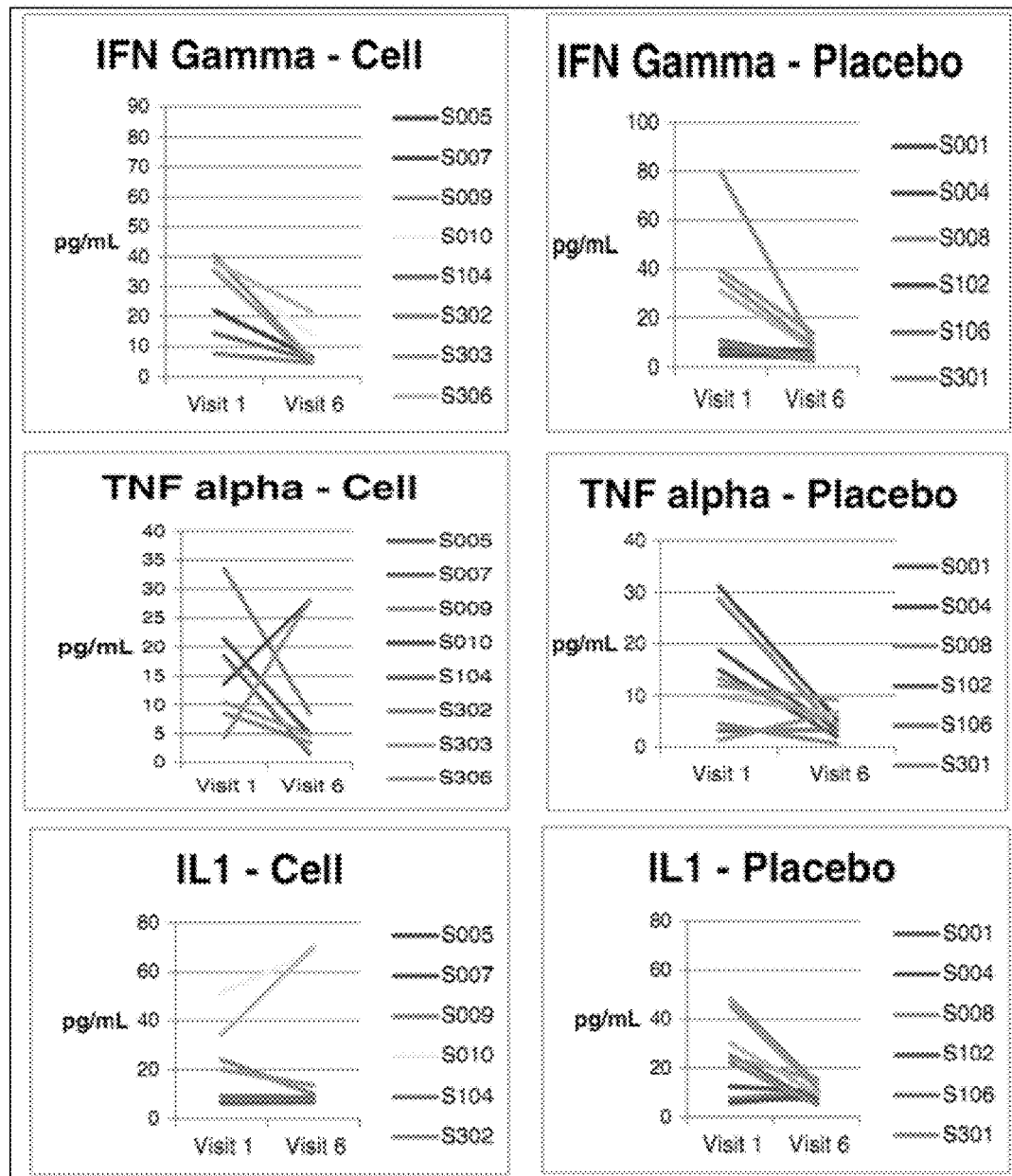

FIG. 23 depicts the graphical representation of Immunological profile (IFN-gamma, IL-1 & TNF-alpha levels) of patients in instant composition treatment (in figure as cell) and placebo.

Figure 24:
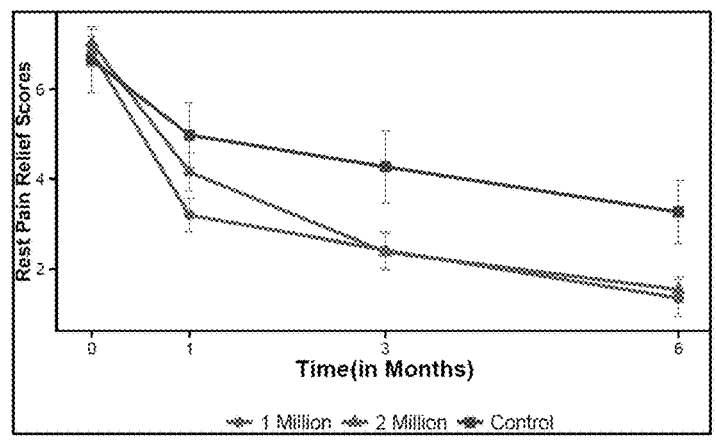

FIG. 24 depicts the graphical representation of Rest pain relief scores post treatment with instant composition, by group with SE Error Bars. X-axis (visit in months): visit 1: 0, visit 4: 1, visit 5: 3 and visit 6: 6Y-axis: Rest pain mean+/−standard error (cm).

Figure 25:
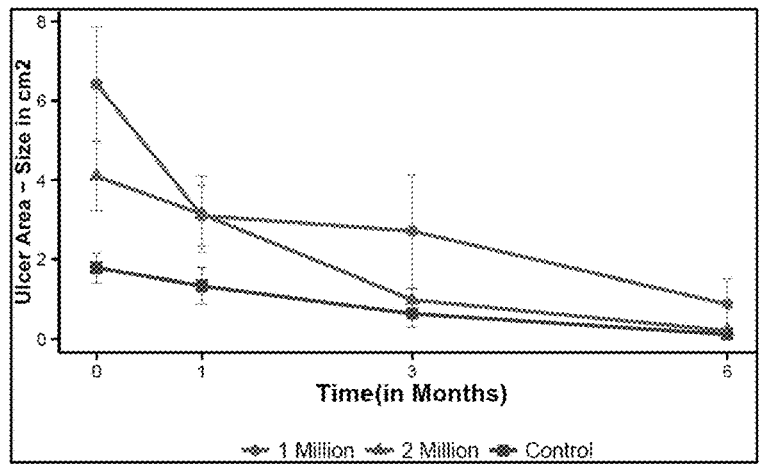

FIG. 25 depicts the graphical representation of reduction in size of Ulcer Area post treatment with instant composition, by group with SE Error Bars (X-axis (visit in months):

visit 1: 0, visit 4: 1, visit 5: 3 and visit 6: 6; Y-axis: Ulcer area mean+/−standard error (cm2)).

Figure 26:
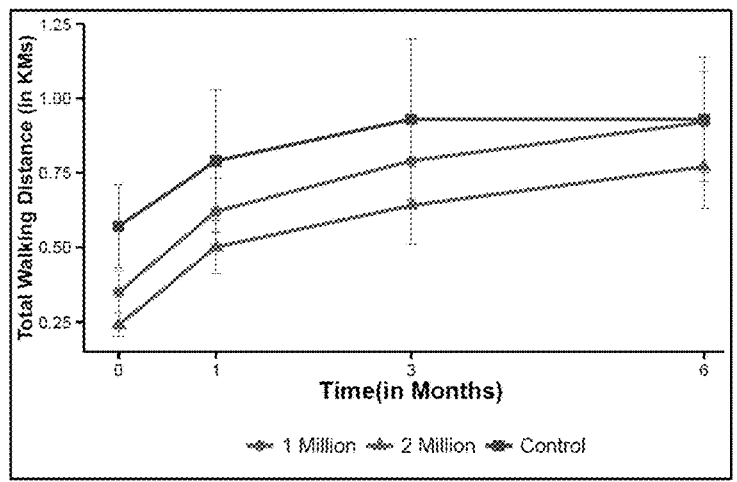

FIG. 26 depicts the graphical representation of total walking distance of subjects, by group with SE Error Bars. (X-axis (visit in months): visit 1: 0, visit 4: 1, visit 5: 3 and visit 6: 6 Y-axis: Total walking distance mean+/−Standard error (km)).

Figure 27:
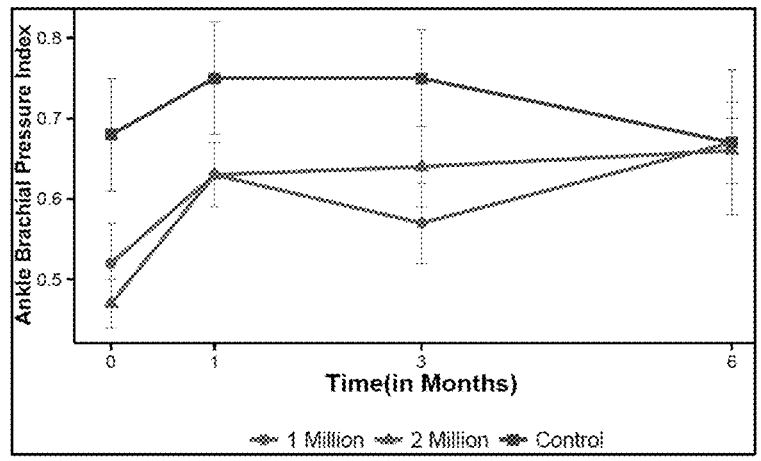

FIG. 27 depicts the graphical representation of increase in Ankle brachial pressure index post treatment with instant composition, by group with SE Error Bars. (X-axis (visit in months): visit 1: 0, visit 4: 1, visit 5: 3 and visit 6: 6; Y-axis: Ankle brachial pressure index mean+/−standard error).

Figure 28:
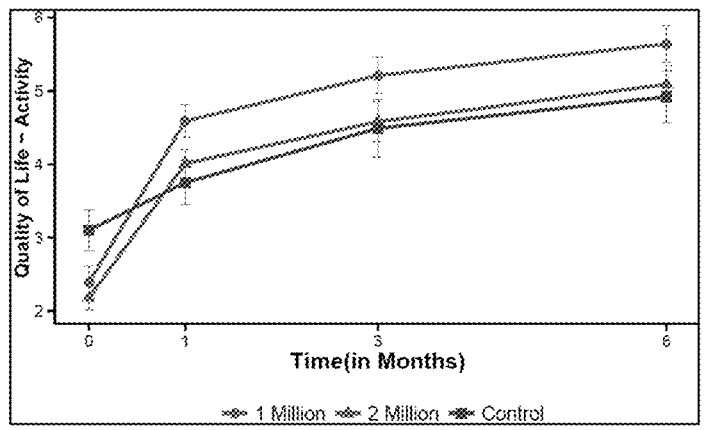

FIG. 28 depicts the graphical representation of enhancement in Quality of life—Activity post treatment with instant composition, by group with SE Error Bars (X-axis (visit in months): visit 1: 0, visit 4: 1, visit 5: 3 and visit 6: 6; Y-axis: Quality of life−Activity mean+/−standard error)).

Figure 29:
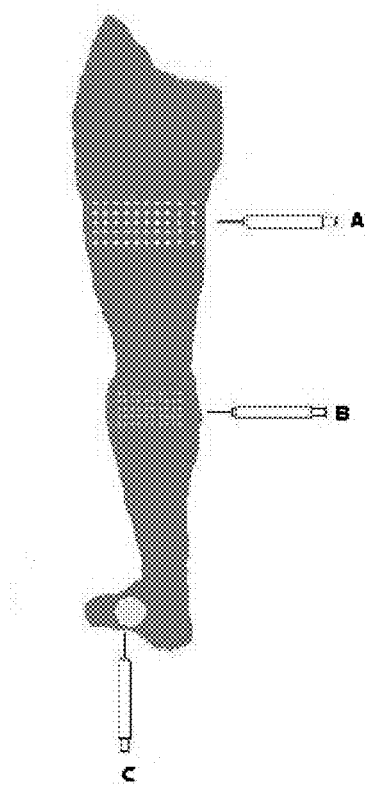

FIG. 29 depicts the different areas (individual and combinatorial) of intramuscular route of administration of the composition. It represents the combinatorial IM administration via thigh muscle (A), calf (B), and local administration at the ulcer (C). Single dose of the instant composition is injected intramuscularly at a grid measuring about 10 cm×6 cm at the calf and thigh muscle region. The figure also indicates single dose intramuscular administration at multiple sites on calf/thigh (40-60 injections). Further, the instant composition is injected locally at a volume of 2 ml around the ulcer (C).

Figure 30:

FIG. 30 depicts the BM-MSCs/instant composition being locally administrated at the site of injury/lesion/ulcer caused by ischemia and the healing in the trial patients.

DETAILED DESCRIPTION OF THE DISCLOSURE

The present disclosure relates to a composition for managing ischemia comprising pooled and expanded allogeneic mesenchymal stromal cells in an amount ranging from about 1 million cells to 1000 million cells, optionally along with pharmaceutically acceptable excipient.

The present disclosure also relates to a method of managing ischemia in a subject having or suspected of having the ischemia, said method comprising acts of administering a composition comprising pooled and expanded allogeneic mesenchymal stromal cells at a dose ranging from about 0.5 million cells per kg of body weight of the subject to 5 million cells per kg of body weight of the subject, optionally along with pharmaceutically acceptable excipient to the subject.

In an embodiment of the present disclosure, the mesenchymal stromal cells are derived from a source selected from a group comprising bone marrow, adipose tissue, wharton's jelly and dental pulp, or any combination thereof, preferably bone marrow.

In another embodiment of the present disclosure, the dose of the mesenchymal stromal cells range from about 1 million cells per kg to 2 million cells per kg of body weight of the subject.

In yet another embodiment of the present disclosure, the mesenchymal stromal cells are obtained by ex-vivo cell culturing; and wherein at least 80% mesenchymal stromal cells are positive for cell specific markers CD 73, CD90, CD105 and CD166 cells, and less than 10% mesenchymal stromal cells are negative for markers CD34, CD45, CD133, CD14, CD19 and HLA-DR.

In still another embodiment of the present disclosure, the expansion is carried out by culturing the pooled allogeneic mesenchymal stromal cells for about 3 to 6 passages.

In an embodiment of the present disclosure, the pooled allogeneic mesenchymal stromal cells induce neovascularization at the administered site.

In another embodiment of the present disclosure, the pharmaceutically acceptable excipient is selected from a group comprising carrier, cyropreservant, serum and pre-formulated ready to use cryopreservation mixture, or any combination thereof; and wherein the carrier is multiple electrolyte injection, Hank's balanced salt solution (HBBS), saline, Lactated Ringer's Injection; the cyropreservant is Dimethyl Sulfoxide (DMSO), the serum is human serum albumin (HSA), and the pre-formulated ready to use cryopreservation mixture is animal protein-free defined cryopreservation medium.

In yet another embodiment of the present disclosure, the ischemia is limb ischemia, ischemic cardiomyopathy (ICM), ischemic stroke, ischemic ulcers or a combination thereof.

In another embodiment of the present disclosure, the ischemia is critical limb ischemia (CLI); and wherein said CLI is a result of Buerger's disease, peripheral artery disease (PAD), or a combination thereof.

In another embodiment of the present disclosure, the subject is mammal. In a preferred embodiment the mammal subject is human.

In another embodiment of the present disclosure, the composition is administered as a single dose at multiple sites through modes selected from a group comprising intramuscular administration, local administration, intravenous administration, intra articular administration, pancreatic duodenal artery administration, intraperitoneal administration, intra cardiac administration, intra cranial administration and hepatoportal administration, or any combination thereof.

In another embodiment of the present disclosure, the said composition is administered intramuscularly; and wherein said intramuscular administration comprises administration at calf muscle region, administration at thigh region, administration at or along or in the course of claudicated vessel, administering locally at or near the site affected by the ischemia, or any combination of intramuscular mode of administration thereof.

In yet another embodiment of the present disclosure, the management is characterized by a parameter selected from a group comprising reduction in rest pain, healing of ulcer, healing of necrosis, healing of gangrene, healing of lesion, healing of wound, or any combination thereof.

In still another embodiment of the present disclosure, the management is characterized by a parameter selected from a group comprising increase in ankle pressure, increase in ankle brachial pressure index (ABPI), increase in transcutaneous partial oxygen pressure (TcPO2), increase in vasculogenesis, or any combination thereof.

In an embodiment of the present disclosure, the method further comprises topical administration of a conditioned medium to a site affected by the ischemia, and wherein said administration of the conditioned medium is carried out either simultaneously or sequentially with the administration of the composition.

In another embodiment of the present disclosure, the conditioned medium is derived from pooled and expanded allogeneic mesenchymal stromal cells, and said conditioned medium comprises cytokine factors selected from a group comprising VEGF, Ang1 and TGF □, or any combination thereof.

In yet another embodiment of the present disclosure, the conditioned medium induces neovascularization at the administered site.

In another embodiment of the present disclosure, the composition or the conditioned medium is formulated as a formulation selected from group comprising aqueous suspension, cream, lotion, gel, emulsion, drop, emulsion in hard or soft gel capsule, elixir, lyophilized cell powder and cell spray or any combinations thereof, preferably aqueous suspension.

In another embodiment of the present disclosure, the composition stays for a time-period of about 1 to 28 days at the site affected by the ischemia leading to the management of ischemia.

The present disclosure relates to a kit for treating ischemia in a subject in need thereof comprising the composition optionally along with: (a) a conditioned medium derived from pooled allogeneic mesenchymal stromal cells wherein said conditioned medium comprises bioactive factors selected from a group comprising VEGF, Ang1, and TGF β, or any combination thereof, or (b) an instruction manual, or a combination of (a) and (b) thereof.

The present disclosure also relates to a composition comprising pooled and expanded allogeneic mesenchymal stromal cells in an amount ranging from about 1 million cells to about 1000 million cells, optionally along with pharmaceutically acceptable excipient for use as a medicament.

The present disclosure relates to a composition, effective dosage and route of administration for managing/treating ischemic conditions and/or vascular disorders, or further deteriorating ischemic conditions and/or vascular disorders.

The present disclosure discloses the use of stem cell therapy for management of ischemic disease affecting extremities of hands, feet and legs due to the restricted blood flow. Further, the present disclosure discloses an effective dosage and route of administration of stem cell composition for neovascularization and thus management of ischemic disease conditions.

The present disclosure relates to a composition comprising 'pooled', 'ex-vivo' expanded and 'allogeneic' mesenchymal stromal cells (MSCs), its effective dosage and route of administration for management of ischemic conditions.

The present disclosure also relates to the employment of stem cell therapy and conditioned medium simultaneously.

In an exemplary embodiment of the present disclosure, the conditioned medium and the stem cell therapy is employed simultaneously for the treatment of CLI. In another exemplary embodiment, the conditioned medium and the stem cell therapy is employed sequentially for the treatment of CLI.

As used herein, the terms MSC, "mesenchymal stromal cell" and "mesenchymal stem cell" are employed interchangeably within the instant disclosure.

As used herein, the terms "cell composition", "Investigation Medicinal product (IMP)", "Investigational product (IP)", "final composition", "final MSC composition", "final therapeutic composition", "composition of the present disclosure", "cell product" and "Stempeucel®" as used in this disclosure means the cell product comprising pooled MSC in a cryopreservation medium/solution.

As used herein, the term "cryopreservation formulation/solution" means a composition/solution used for preservation of cells for longer duration/shelf life. The alternate terms used are 'freeze media', 'freezing mixture', 'pre-formulated ready to use perseveration mixture' all of which shall mean cryopreservation/solution. More specifically, in the present disclosure, MSCs are cyropreserved using a cryopreservation solution/formulation which comprises of serum, carrier and cryoprotectant. In yet another embodiment of the present disclosure, the MSCs are cryopreserved using commercially available pre-formulated ready to use preservation mixture or solution. The cell composition is cryopreserved in liquid nitrogen at −196° C. until use. On requirement, the cells are thawed and used as per the patient dosage requirement decided by the clinician.

As used herein, the term "excipient" means an inert substance used as vehicle and/or diluent for the active ingredient. It is a substance added to a formulation to provide benefit of the processing or cryo-protection of active ingredient and is intended to be present in the final product as an inactive ingredient. Excipient includes but is not limited to physiological solution, multiple electrolyte injection, Hank's balanced salt solution (HBB S) solution, saline, Lactated Ringer's Injection, cryoprotectant and so on.

As used herein, the term 'pooling' or 'pooled' in the context of mesenchymal stromal cells means combining the mesenchymal stromal cells of multiple donors i.e. more than one donor.

As used herein, "management" or "managing" refers to preventing a disease or disorder from occurring in a subject, decreasing the risk of death due to a disease or disorder, delaying the onset of a disease or disorder, inhibiting the progression of a disease or disorder, partial or complete cure of a disease or disorder and/or adverse effect attributable to the said disease or disorder, obtaining a desired pharmacologic and/or physiologic effect (the effect may be prophylactic in terms of completely or partially preventing a disorder or disease or condition, or a symptom thereof and/or may be therapeutic in terms of a partial or complete cure for a disease or disorder and/or adverse effect attributable to the disease or disorder), relieving a disease or disorder (i.e. causing regression of the disease or disorder). Further, the present disclosure also envisages treating the said disorder by administering therapeutically effective/efficacy dosage of the composition comprising of pooled allogeneic Mesenchymal Stromal cells along with suitable carriers/excipient. The disclosure further includes unique and effective routes of administration in order to obtain effective healing at the site of gangrene injury/inflammation/wound/ulcers by forming new blood vessels.

In an embodiment of the present disclosure, the term 'simultaneously' used in the context of application of conditioned medium means that the conditioned medium and the stem cell therapy is employed in combination at the same time for treatment of CLI. Said combination refers to employing conditioned medium and stem cell therapy individually at the same time, or employing conditioned medium and the stem cell therapy together at the same time.

In another embodiment of the present disclosure, the term 'sequentially' used in the context of application of conditioned medium means that the conditioned medium and the stem cell therapy is employed in an order one after the other, wherein the application of conditioned medium can be preceded by stem cell therapy or vice versa for treatment of CLI.

In an embodiment of the present disclosure, the bone marrow is obtained from a cell bank. The term "Bank" in the present disclosure means source for obtaining the bone marrow. In an embodiment, such source is pre-processed and/or cryopreserved bone marrow, stored for instant or future use. In an embodiment, the source is mono-nuclear cell (MNC) bank. In another embodiment, the source is a Mesenchymal Stem Cell Bank. In embodiments of the disclosure, any depository that stores bone marrow for a pre-determined period of time is a bank. Further, any medium such as apparatus or device or vessel or container that stores bone marrow for a pre-determined period of time is considered to be a bank. In an embodiment, information about the bank is procured from bone marrow registry.

It is to be noted here that in the present disclosure, isolating or obtaining mesenchymal stem cells from a donor does not involve operation or surgery or any invasive means/methods performed by doctors or medical practitioners. In other words, a person having average skill in the field of stem cell technology can obtain or isolate mesenchymal stem cells using means which does not involve or require invasive steps (such as surgery) or the intervention of a doctor or a medical practitioner. For instance, in an embodiment of the present disclosure, bone marrow derived mesenchymal stem cells (BM-MSCs) are obtained by processing of bone-marrow which do not involve any surgical process. In another embodiment, stem cells (BM-MSCs) are obtained from sources including but non-limiting to stem cell banks (a repository of stem cells), as gifts from collaborating laboratories or a scientific person in this field of technology, and so on, and the same does not include any surgical/invasive step for obtaining said stem cells. Further, all the aforementioned approaches or sources of isolating/obtaining stem cells are within the scope of the present disclosure.

Human MSCs are present as a rare population of cells in bone marrow, representing 0.001 to 0.01% of the nucleated cells, but they rapidly grow in culture without losing their stemness. MSCs can be expanded in vitro ≥2 million fold and retain their ability to differentiate into several mesenchymal lineages. MSCs differentiate not only into mesodermal lineage such as bone, cartilage and adipose tissue but also trans-differentiate into other lineages like neurons and endothelial cells.

Adult MSC do not express human leukocyte antigen (HLA) class II antigens of the cell surface and do not elicit a proliferative response from allogeneic lymphocytes, thus proving that the cells are not inherently immunogenic. The MSCs also do not express co-stimulatory molecules CD80, CD86, CD40 or CD31 (PECAM-1), CD18 (LCAM) and CD56 (NCAM-1) and hence do not activate allo-reactive T cells. The cell composition of the present disclosure comprise allogeneic MSCs which do not induce lymphocyte proliferation when used in a mixed lymphocyte reaction (MLR), which is an in-vitro model of immune cell activation.

In an embodiment of the present disclosure, the MSCs are derived from various sources including but not limited to Bone marrow, Adipose tissue, Wharton's jelly, Dental pulp and so on. In a preferred embodiment, the source of MSCs is Bone marrow. In another embodiment of the present disclosure, the MSCs are allogeneic and pooled in nature. Bone marrow derived MSCs have several non-limiting advantages such as:
a. Non embryonic source
b. Non-tumorigenic
c. Ease of isolation
d. High expansion potential
e. Immune privileged
f. Genetic stability
h. Reproducible characteristics
i. Compatibility with tissue engineering principles
j. Potential to enhance repair in many vital tissues.

Ischemia condition is the result of inadequate arterial blood flow to any area in the body. The arterial circulation ensures supply of oxygen and nutrients to all the cells. Constriction of the vessels leads to organ or tissue damage thus resulting in ischemic conditions. Ischemic condition can be caused by blood clot such as thrombi or emboli which can block the flow of blood through that vessel. Some other causes of ischemia also include vasculitis, atherosclerosis, coronary artery disease and peripheral artery disease.

There are various types of ischemia, depending on the area where it affects. Peripheral arterial disease (PAD) comprises atherosclerosis of the abdominal aorta, iliac, and lower-extremity arteries. Patients with PAD may experience a multitude of problems, such as claudication, ischemic rest pain, ischemic ulcerations, repeated hospitalizations, revascularizations, and limb loss. Critical limb ischemia (CLI) is the most severe form of peripheral arterial disease (PAD) caused by chronic inflammatory processes associated with atherosclerosis that result in markedly reduced blood flow to the legs, feet and hands. Symptoms of CLI include severe pain, skin ulcers or skin sores or gangrene. Further, Critical limb ischemia is also involved with Buerger's disease. Other type of ischemia includes myocardial ischemia caused due to restricted blood flow to the heart muscle due to blockage of a coronary artery. Another type of ischemia can occur in brain's arteries known as cerebral ischemia. Yet another example of ischemia condition is Ischemic cardiomyopathy (ICM), ischemic stroke and Ischemic ulcers.

The present disclosure also relates to the management of PAD. Further, Critical Limb Ischemia (CLI) in the present disclosure refers to the signs and symptoms of Buerger's disease (Thromboangitis obliterans), and atherosclerotic lower limb disease known as peripheral arterial disease (PAD) or peripheral vascular disease (PVD) or peripheral artery occlusive disease (PAOD). Buerger's disease is caused by blockage in the blood vessels of limbs (feet and arms). The clot formation and inflammation of the vessels reduces the blood supply to the limbs, thus causing tissue damage and death leading to severe pain. It is strongly associated with use of tobacco.

Peripheral artery disease (also called peripheral arterial disease) is a common circulatory problem in which narrowed arteries reduce blood flow to the limbs. Peripheral artery disease (PAD), affects the extremities—usually legs. As a result, these regions don't receive enough blood flow to keep up with demand. This causes symptoms, most notably leg pain when walking (intermittent claudication). Peripheral artery disease is also likely to be a sign of a more widespread accumulation of fatty deposits in arteries (atherosclerosis). This condition can also reduce blood flow to heart and brain, as well as legs.

In an exemplary embodiment of the present disclosure, the most prominent features of critical limb ischemia (CLI) arising from Buerger's disease and/or atherosclerosis PAD include one or any combination of symptoms selected from severe rest pain in the legs and feet while a person is not moving; non-healing sores on the feet or legs; pain or numbness in the feet; shiny, smooth, dry skin of the legs or feet; thickening of the toenails; absent or diminished pulse in the legs or feet; open sores, skin infections or ulcers that do not heal; dry gangrene (dry, black skin) of the legs or feet. The symptoms of CLI therefore include any injury/inflammation/wound/ulcers of the limb and any of these terms may be used interchangeably to mean or refer to a symptom/characteristic of CLI.

In another aspect the present disclosure, the ischemia condition in the present disclosure also refers to Ischemic cardiomyopathy (ICM).

In the present disclosure, the pooled allogeneic population of MSCs in the composition have cells which are at least 80% positive for CD73, CD105, CD90, CD166 and cells that express less than 10% CD34, CD45, CD155, CD14, CD19, HLA-DR.

In the present disclosure, the cell composition is administered via intramuscular (IM) route through gastrocnemius muscles (calf muscle) or thigh muscle (FIG. 29).

In another embodiment of the present disclosure, the cell composition is administered through a combination of IM route via gastrocnemius muscle (calf muscle) or thigh muscle and local injection at the gangrene/ulcer/wound/site of injury.

In another embodiment, the cell composition is administered by IM route via. a combination of administration at or near or along or in the course of the blocked/constricted/claudicated vessel and local administration around the ulcer/gangrene/lesion/wound (FIG. 29).

In another embodiment, the cell composition is administered by IM route via. a combination of administration at or near or along or in the course of the claudicated vessel and administration at calf muscle.

In another embodiment of the present disclosure, cell composition is injected intramuscularly around at or near or along or in the course of the constricted/claudicated vessel. In yet another embodiment, the cell composition is injected intramuscularly around the constricted/claudicated vessels in combination with other routes of administration to efficiently manage the ischemic/vascular conditions.

In another embodiment, the claudication in ischemia is due to constriction, blockage or obliteration of blood vessels.

In an embodiment, the anti-inflammatory effect of the instant cell composition reduces pain due to inflammation at the site of injury.

Injury or inflammation is a prerequisite for the participation of stem cells to home and differentiate on to this micro-environment. The increased vascular permeability and expression of adhesions like proteins like integrin assist in stem cell homing. The migratory capacity of stem cells is dependent on natural growth factors such as VEGF, stromal cell derived factor-1 (SDF1) and stem cell factor (SCF). The expression of VEGF, SDF1 and SCF is highly unregulated in the hypoxic damaged tissue and is responsible for the recruitment of the stem cells to assist in the repair mechanism.

In the present disclosure, the unique routes of administering the cell composition help in managing the ischemic conditions by reducing the rest pain and therapeutically healing the ulcers.

The method of administration of the cell composition used in the instant disclosure is of prime importance which helps in direct homing of cells at the site of injury in addition to the intrinsic homing ability of the injected cells. Thus, the clinical outcome is more effective and significant for managing the ischemic conditions.

In an embodiment of the present disclosure, the MSCs of the cell composition facilitate neovasculazation by increasing vascular endothelial growth factor (VEGF) levels. Further, the MSCs display membrane-bound and soluble secreted molecules involved with cell attachment to neighbouring cells and to the extra cellular matrix. The cell surface expressions of MSCs enable them to home from bloodstream to mesenchymal tissue.

The potential beneficial mechanisms of action of using mesenchymal stem cell therapy in CLI are the regeneration potential of MSCs viz.

Neo-angiogenesis—which helps in development of new collateral blood vessels and thereby improves circulation or microcirculation in the ischemic region; and Myogenesis—regeneration of damage skeletal muscle.

In an embodiment, adult stem cells derived from bone marrow contain not only endothelial progenitor cells (EPCs) but also angiogenic factors and cytokines and the implantation of present BM-MSCs into ischemic tissues augment collateral vessel formation.

In an embodiment, the cell composition of the present disclosure shows low immunogenicity and this aspect has been demonstrated/validated in-vivo in animal models using infusion of pooled and allogeneic MSCs.

In another embodiment, the injections of pooled and allogeneic MSCs do not stimulate the formation of allospecific antibodies and do not lead to T-cell sensitization of the recipient to alloantigen in different animal models. Studies have also shown that the MSCs possess the ability to engraft, persist and function in an unrelated mismatched allogeneic host.

In an exemplary embodiment of the present disclosure, the stem cell therapy (pooled and allogeneic mesenchymal stromal cells) for the management of CLI is employed along with the application of conditioned medium obtained from culturing of said mesenchymal stromal cells. Said conditioned medium is rich in bioactive factors such as cytokines, growth factors etc. secreted by the cells. The conditioned medium is applied topically on the site of wound/inflammation/gangrene for enhancing the efficacy of cell therapy in the CLI management. The application of conditioned medium along with cell therapy results in a synergistic effect, thus providing an improved management of CLI. In an embodiment, the bioactive factors contained in the conditioned medium include but is not limited to cytokines/growth factors selected from a group comprising VEGF, Ang1, AGPT1, TGF □, IL-8, CXCL5, FGF and HGF.

In an exemplary embodiment as mentioned above, the conditioned medium and the stem cell therapy is employed simultaneously for the treatment of CLI. In another exemplary embodiment, the conditioned medium and the stem cell therapy is employed sequentially for the treatment of CLI.

In another embodiment of the present disclosure, the composition or the conditioned medium is formulated as a formulation selected from group comprising aqueous suspension, cream, lotion, gel, emulsion, drop, emulsion in hard or soft gel capsule, elixir, lyophilized cell powder, bandage and cell spray, or any combination thereof. In a preferred embodiment, the composition or the conditioned medium is formulated as an aqueous formulation.

In an exemplary embodiment of the present disclosure, a composition comprising allogeneic, ex-vivo cultured and pooled mesenchymal Stromal cells (MSCs) derived from bone marrow is disclosed. The said composition is administered in specific dosage ranges and routes for managing/treating limb ischemia patients. Further, the said therapeutic composition possess both myogenic and angiogenic properties and is successfully proven to have improved efficacy in managing CLI.

The MSCs are derived from bone marrow of multiple healthy donors with proper informed consent and approval. In an embodiment of the present disclosure, the MSCs are derived from human donors selected from male, female, or a combination thereof. In another embodiment, the number of donors is at least two. In yet another embodiment, the number of donors is three, four, five, six, seven, eight, nine or ten and so on, as suitable.

In an exemplary embodiment, the MSCs from at least two or more donors is pooled to prepare the cell composition of the present disclosure.

In a specific embodiment of the present disclosure, the allogeneic pooled Mesenchymal Stromal Cells (MSCs) possess numerous advantages when compared to single donor derived MSCs. Pooled MSC composition of the present disclosure have significantly improved immunomodulatory characteristics thus ensuring that there is minimal biological variability/immunological reaction in the recipient post administration of pooled MSC composition.

The pooled and expanded MSC's of the composition of the present disclosure are characterised by greater than about 80% positivity for BM-MSC's associated markers CD73, CD90, CD166 and CD105 and less than about 10% positivity for CD14, CD19, CD155, CD34, CD45, and HLA-DR, and also negative for co-stimulatory molecules including but not limiting to CD markers like CD40, CD80 and CD86.

Cell composition of the present disclosure efficiently differentiates in-vitro to osteogenic, chondrogenic and adipogenic cells and also possesses strong immune-modulatory/immunosuppressive, and anti-inflammatory activity. The composition is also non-immunogenic in nature i.e. the composition does not elicit an immune response in a subject post administration of the same.

The Cell composition secretes a variety of bio active factors with diverse functional activity especially those that have been implicated in angiogenesis including but not limiting to VEGF, TGF-β, HGF, Angiopoeitin 1 and 2, and IL-8 among others. In particular, VEGF secreted by the cell composition has been shown to cause the migration, proliferation and angiogenesis of endothelial cells in-vitro. The strong angiogenic and immunomodulatory activities exerted by the cell composition indicate that these cells are of significant therapeutic value in improved treatment of CLI patients.

The various non-limiting advantages of using the cell composition comprising pooled and expanded MSC along with the carriers/excipient are as follows:
a. Individual variability minimized;
b. Consistent non-immunogenic & immunosuppressive properties;
c. Broader Cytokine/Growth Factor (GF) array;
d. Increased potential for various disease indications;
e. Large product doses compared to single donor.

In an embodiment of the present disclosure, the pooled bone marrow derived mesenchymal stem cells (BM-MSCs) result in highly efficacious BM-MSCs compositions. The pooled BM-MSC composition of the present disclosure possess high expression of angiogenic factors and has high proliferative capacity, thereby providing significantly improved efficacy in the management of ischemia along with generating higher quantity of product. On the contrary, the stem cell compositions obtained from individual donors result in lower expression of angiogenic factors, and due to their poor proliferation, the quantity of final product obtained is also lower. Thus, the present disclosure provides for pooled BM-MSCs compositions which have higher expression of angiogenic factors as well as higher proliferation in comparison to non-pooled compositions, and show improved efficacy in the treatment of ischemic conditions such as CLI.

Figure 5:
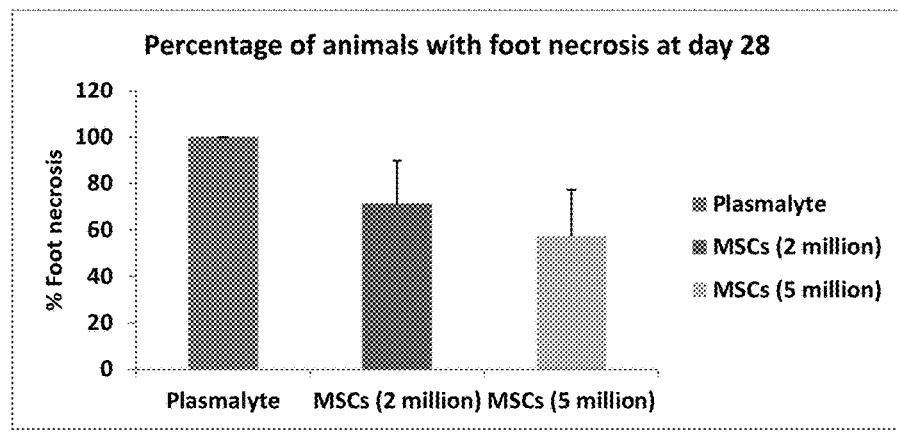
FIG. 5 depicts the percentage of animals with foot necrosis at day 28 after hind Limb Ischemia (LI) induction in LI+vehicle control, LI+$2\times10^6$ and LI+$5\times10^6$ BM-MSCs treated group animals.

In another embodiment of the present disclosure, the pooled bone marrow derived mesenchymal stromal cells (BM-MSCs) stay for a much longer period of time in the ischemic area compared to the same non-ischemic area of normal subject, and accordingly contributes to the improved efficacy in ischemic treatment. In an embodiment, the pooled BM-MSCs stay for a time-period ranging from about 1 to 28 days. Most of the signal intensity disappears around day 28, which establishes that the cells are eliminated from the system. Since the blood flow is restored in the affected limb, the foot necrosis reduces significantly (p<0.001) by day 28 (FIG. 5). In addition, no cells are detected in any other organ of the animals and the cells predominantly stay at the affected site, i.e. in the hind limb muscle (FIG. 17).

The present disclosure further relates to a composition comprising allogeneic pooled mesenchymal stromal cells, wherein the mesenchymal stromal cells are in an amount ranging from about 1 million cells to 1000 million cells.

The formulation or composition of the present disclosure employed towards management of ischemia comprises pooled MSCs along with excipients namely 'Multiple Electrolytes Injection (carrier)' such as PlasmaLyte-A, 'cryoprotectant' such as DMSO and 'Serum' such as human serum albumin (HSA). For administration purpose, said composition/formulation is further diluted with carrier/vehicle [such as multiple electrolyte injection (PlasmaLyte-A), physiological solution Hank's balanced salt solution (HBBS) solution, saline, Lactated Ringer's Injection, cryoprotectant] and employed for administration.

In an alternate embodiment, the formulation or composition comprises pooled MSCs along pre-formulated ready use commercial cyropresevation mixture selected from a group comprising CryoStor® family—a commercially available animal protein-free defined cryopreservation formulation from Biolife Solutions such as: 'CyroStor5 (CS5)' [an optimized freeze media pre-formulated with 5% DMSO], 'CyroStor10 (CS10)' [an optimized freeze media pre-formulated with 10% DMSO], 'CyroStor2 (CS2)' [an optimized freeze media pre-formulated with 2% DMSO] and 'hypothermosol', wherein said composition/formulation is further diluted with carrier/vehicle (such as PlasmaLyte-A) and employed for administration purpose.

In a preferred embodiment, the cell composition is prepared by employing pooled mesenchymal stromal cells, human serum albumin, plasmaLyte-A and DMSO wherein, the said cell composition is further diluted using a carrier/vehicle such as PlasmaLyte-A to obtain the final cell composition for administration. In another preferred embodiment, pooled Mesenchymal stromal cells are cryopreserved in commercially available pre-formulated ready to use preservation mixture such as cyrostor-5 (CS5), CyroStor10 (CS10), CyroStor2 (CS2) and/or hypothermosol wherein, the said cell composition is further diluted using a carrier/vehicle for administration.

As described above, the pooled Mesenchymal Stromal Cells of the present disclosure are either in combination with excipients selected from a group comprising carrier, serum and cryopreservant, optionally along with other pharmaceutically acceptable excipients/additives OR the cell composition comprises pooled Mesenchymal Stromal Cells in a pre-formulated ready to use preservation mixture such as cyrostor-5 (CS5), CyroStor10 (CS10), CyroStor2 (CS2) and/or hypothermosol.

In an embodiment, cell product dosage ranges from about 100 to 200 million cells in 4-15 ml of the cyropreservation solution (i.e. serum+carrier+cryopreservant OR pre-formulated ready to use preservation mixture).

In another embodiment, cell dosage to be injected to the patient is decided by the clinician depending on various parameters such as weight, age, manifestation of disease condition etc. of the patient, preferably based on the weight of the patient.

In yet another embodiment, the IMP composition is cryopreserved in 15 ml of freezing media. Thereafter, at the time of administration, the cryobags are thawed and mixed with physiologically compatible carrier (volume of 35 ml) to make a total volume of 50 ml.

The present disclosure also provides the dosage of pooled MSCs for management of ischemia. In the final MSC composition which is to be administered for management of ischemia, the dosage of pooled MSCs range from about 0.5 million cells/kg body weight to about 5 million cells/kg body weight. In a preferred embodiment, the dosage of pooled MSCs is 1 million cells/kg body weight, 2 million cells/kg body weight, 3 million cells/kg body weight, 4 million cells/kg body weight or 5 million cells/kg body weight. In a most preferred embodiment, the dosage of MSCs in the final MSC composition is 2 million cells/kg body weight.

In an embodiment, the effective cell dose/cell composition of the present disclosure for local administration around/near/adjacent to the site of ulcer/gangrene/injury/inflammation/wound is in the range of about 2-30 million cells of the ulcer area. In another embodiment, the effective cell dose/cell composition of the present disclosure for local administration around/near/adjacent to the site of ulcer/gangrene/injury/inflammation/wound is in the range of about 2-8 million cells/cm$^2$ of the ulcer area. The dose for local administration will be established by the physician based on the size/area of the ulcer/ischemic wound. The local administration is achieved via. route including but not limiting to intramuscular, subcutaneous, intradermal, or any combination thereof.

In an embodiment of the present disclosure, the effective therapeutic dose of the pooled and expanded mesenchymal stromal cells range from about 1 million cells to 1000 million cells.

The present disclosure provides the route of administering composition comprising pooled MSCs for management of ischemia. In an embodiment of the present disclosure, the MSC compositions are administered through modes selected from a group comprising intramuscular administration, intravenous administration, intra articular administration, pancreatico duodenal artery administration, hepatoportal, subcutaneous administration, intradermal administration, intra cardiac administration, intra cranial administration and injection in any other appropriate part, or any combination thereof. In a preferred embodiment, the route of administration employed is intramuscular, wherein the intramuscular route comprises administration in the calf muscle region or locally around the site/near the site/at the site of gangrene/injury/inflammation/wound/ulcer (periwound). In a more preferred embodiment, the route of administration is 'intramuscular', wherein said intramuscular route comprises of a 'combination' of administration in the calf, thigh muscle and locally around the site/near the site/at the site of injury/inflammation/wound/ulcer/gangrene (FIG. 29 and FIG. 30).

In yet another embodiment of the present disclosure, CLI is treated by administrating cell composition intramuscularly in the calf muscle region and locally around the site/near the site/at the site of injury/inflammation/wound/ulcer/gangrene in combination with the topical application of conditioned medium [which is obtained and processed from the culturing of pooled MSCs] rich in bioactive factors including but not limiting to angiogenic factors, growth factors and cytokines. The angiogenic factors such as Fibroblast Growth Factors (FGF), Angiopoietin 1 (Ang 1) and Vascular Endothelial Growth Factors (VEGF) are important in angiogenesis/formation of new capillaries.

In another embodiment of the present disclosure, the composition is administered as a 'single' dose at multiple sites. In other words, the composition is administered to the subject during a single time frame, but at multiple sites (for instance, in embodiments as described above, the composition can be administered at calf muscle region as well as locally, or multiple injections can be given at calf muscle or locally). In a preferred embodiment, the composition is injected as single dose at the gastrocnemius muscles (calf muscles) through multiple injections comprising of about 40×60 injections and around the ulcer through multiple injections comprising of about 2 to 10 injections.

In an embodiment of the instant disclosure, the mesenchymal Stromal cells (MSCs) are isolated from bone marrow of multiple donors. The MSCs are thereafter passaged to obtain/establish master cell bank composition (MCB) of each donor. Said MCBs comprising MSCs of individual donors are cyropreserved in FBS (fetal bovine serum) and DMSO (dimethyl sulfoxide). Preferably, the MCB comprises MSCs of individual donors cyropreserved in FBS at a concentration of about 90% (v/v) and DMSO at a concentration of about 10% (v/v). The MSCs from multiple MCBs are 'pooled' and subsequently passaged to arrive at working cell bank composition (WCB) comprising pooled and allogeneic MSCs cyropreserved in FBS and DMSO. The said WCB preferably comprises pooled and allogeneic MSCs cyropreserved in FBS at a concentration of about 90% (v/v) and DMSO at a concentration of about 10% (v/v).

The aforesaid WCB is further subjected to passaging/culturing to obtain a final therapeutic composition/cell composition/Investigational medicinal product (IMP)/Investigational product (IP)/Stempeucel®/final MSC composition comprising bone marrow derived pooled and expanded mesenchymal Stromal cells cryopreserved in a cyropreservation solution comprising of Plasmalyte-A, human serum albumin (HSA) and DMSO until further use. Optionally, other pharmaceutically acceptable excipients/additives can be added at the time of administering the composition to a subject.

In a specific embodiment of the present disclosure, the above obtained therapeutic composition comprising pooled and expanded allogeneic mesenchymal stromal cells is employed for the management of ischemic conditions. In a preferable embodiment, the ischemic condition is Critical Limb Ischemia (CLI). In a specific embodiment, the CLI is a manifestation of Buerger's disease. In another embodiment, the CLI is a manifestation of atherosclerotic Peripheral Arterial Disease (PAD). In yet another embodiment, the ischemic condition is ischemic cardiomyopathy (ICM).

In an exemplary embodiment of the present disclosure, the composition comprising pooled and expanded allogeneic mesenchymal stromal cells is employed for the management of critical limb ischemia (CLI). In an embodiment the critical limb ischemia is due to Buerger's disease, Peripheral Arterial Disease (PAD) or combination thereof.

In another embodiment, the Critical Limb Ischemia (CLI) is due to atherosclerotic peripheral arterial disease (PAD).

In an exemplary embodiment of the present disclosure, the composition comprising pooled and expanded allogeneic mesenchymal stromal cells is employed for the management of ischemic cardiomyopathy (ICM).

Thus, the present disclosure aims at providing for bone marrow derived pooled and allogeneic MSC compositions with specific dosage ranges and unique combination of modes of administration for management of ischemic conditions. Said dosage ranges and administration routes result in improved efficacy in managing ischemic conditions by inducing neovasculazation. In exemplary embodiments, said compositions are employed for managing Critical Limb Ischemia (CLI) in a subject in need thereof. The non-limiting critical/advantageous features of the instant disclosure are as follows:

- The use of 'pooled', expanded and 'allogeneic' mesenchymal stromal cells (MSCs) for managing ischemic conditions, preferably critical limb ischemia (CLI);
- The specific route of administering the present MSC composition. The preferable mode of administration is 'intramuscular (IM)'. Further, said IM administration is via. Calf muscle, thigh muscle, at or near the site of injury (local administration), administration at or near or along or in the course of the claudicated vessel, or any combination of IM administration thereof. More particularly, IM administration with a combination of administration at calf, thigh muscle and local administration at or near the site of injury is preferred.
- Administering the composition as a 'single' dose through multiple injections;
- The optional employment of conditioned media comprising bioactive/angiogenic factors along with the present composition to enhance the efficacy of managing ischemic conditions. The said conditioned media is applied either simultaneously or sequentially with the present composition;
- The dosage of MSCs employed for the management of ischemia, preferably CLI. Further, the dosage of MSCs preferably range from about 0.5 million cells/kg body weight to 5 million cells/kg body weight, more preferably about 1-2 million cells/kg body weight;
- Local administration of the composition around/near/adjacent to the site of ulcer/gangrene/injury/inflammation/wound in the range of about 2-30 million cells or about 2-8 million cells/cm² of the ulcer/wound area.
- The pooled MSCs of the present compositions have higher expression of angiogenic factors as well as higher proliferation thus contributing to the improved efficacy in treatment of ischemic conditions;
- The pooled MSCs of the present compositions stay for longer time-periods at the injury site/ischemic site.

While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

Additional embodiments and features of the present disclosure will be apparent to one of ordinary skill in art based upon description provided herein. The embodiments herein and the various features and advantageous details thereof are explained with reference to the non-limiting embodiments in the description. Descriptions of well-known/conventional methods and techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the following examples should not be construed as limiting the scope of the embodiments herein.

EXAMPLE 1

Preparation of Pooled Mesenchymal Stromal Cells Composition

The Investigational Medicinal Product (IMP) or the composition comprising of pooled BM-MSCs (along with the vehicle/excipient) is prepared wherein, the pooled BM-MSCs are obtained from bone marrow aspirates of healthy donors who were not HLA matched to the recipients. The volunteers for bone marrow donation were tested according to 21 Code of Federal Regulations (CFR) 640, FDA donor suitability & ICMR guidelines for healthy bone marrow donor screening.

Mesenchymal stromal cells are isolated/obtained from the donor's bone marrow mononuclear stem cells using density gradient separation method and thereafter cultured. The cells are expanded in-vitro to manufacture the required number of cells and to establish a donor specific master cell bank (MCB) at Passage (P1). MSC isolated from each donor is cryopreserved separately in individual vials and is labeled with the donor number of each donor. MCB comprising of cells so cryopreserved serve as a source of MSCs for future manufacturing of working cell bank (WCB).

The MCB vials of individual donors is thawed for further culturing and pooled in equal proportion to establish working cell bank composition at passage 3 (P3). The working cell banks are maintained for routine upscaling and quality control purposes. The working cell banks are upscaled further to produce the cell composition at about passage 4 (P4) to passage 6 (P6). Once, the desired number of cells is produced, aliquots of samples are provided for quality control testing purposes. These include complete characterization of MSCs by flow cytometry and differentiation capacity of these cells to osteocytes, chondrocytes and adipocytes. In addition, sterility, *mycoplasma*, infectious disease markers testing and endotoxin testing are performed at the level of MCB, WCB and IMP to confirm that the cells are devoid of any microbial contaminants, are sterile and negative for infectious disease markers at each stage of cell expansion. Aliquots of the cells are transferred into liquid nitrogen storage vials for quality testing. Release criteria for pooled BM-MSC cell composition used for administration in the in-vivo study are based on the following:

a) negative results for microbiological testing,
b) endotoxin content of <0.06 EU/ml,
c) cell viability (trypan blue exclusion test) of >85%,
d) pH between 7.2 to 7.4,
e) exhibiting normal DNA ploidy,
f) normal Karyotype,
g) phenotypic marker analysis by flow cytometry as above, and
h) confirmation of differentiation of cells to osteocyte, chrondocyte and adipocyte.

TABLE A

| Investigational Medicinal Product (IMP) specification | | |
|---|---|---|
| Description | Specification | |
| Morphology | Cell are fibroblastic and spindle shaped in active growing condition Cells are intact and round in shape after the tryspin action | |
| Viability | >80% | |
| Cell Phenotype | Positive/high expression markers | Low expression Markers |
| | CD 73 > 80% CD105 > 80% CD 90 > 80% CD 166 > 80% | CD 34 < 10% CD 45 < 10% CD 133 < 10% CD 14 < 10% CD19 < 10% HLA-DR < 10% |

EXAMPLE 2

Figure 1:
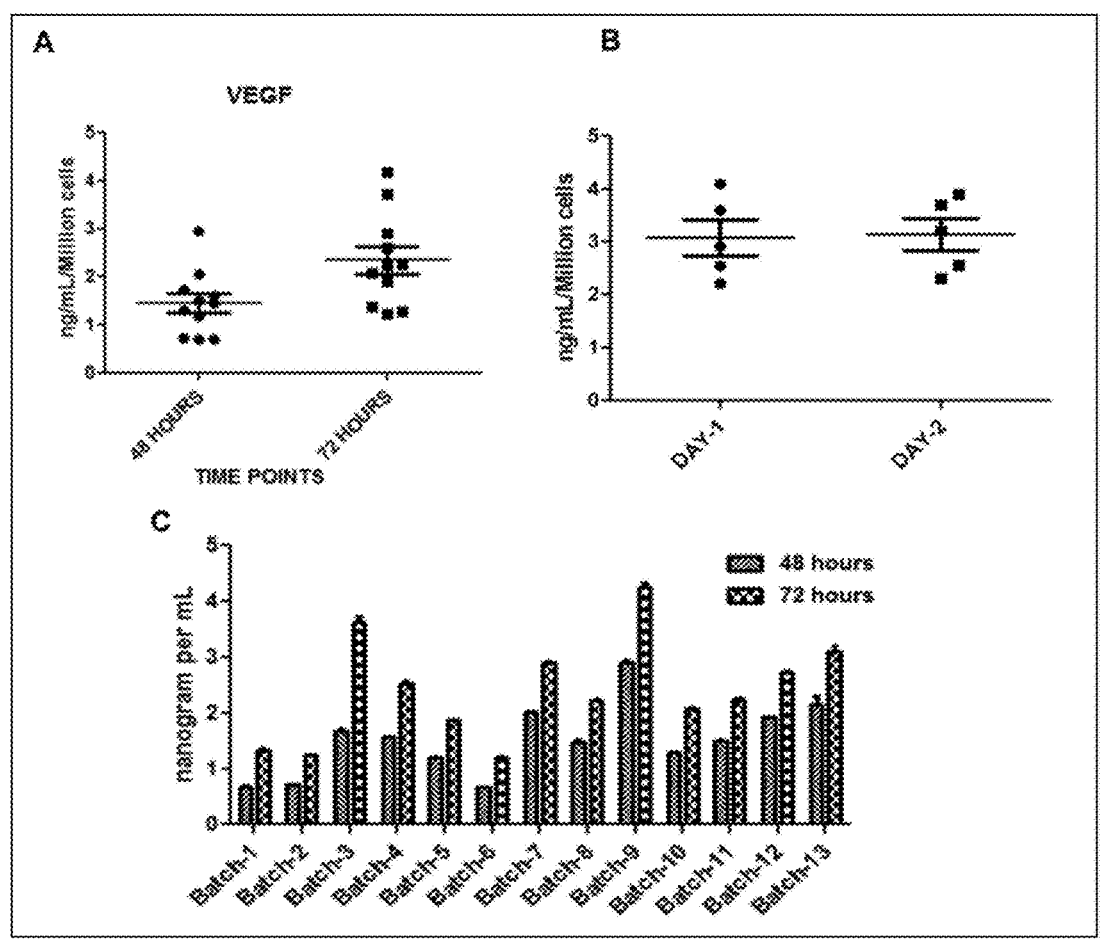
FIG. 1 depicts the results of in-vitro quality check VEGF assay. The levels of VEGF (a potency marker for consistent quality check) in the conditioned medium of the present pooled MSC cell composition/IMP are evaluated.

In-Vitro Assays for Quality Check and Study of Efficacy of MSC Compositions (A) VEGF is a potent pro-angiogenic factor and consistently gets expressed over the passages. Hence, VEGF is selected as a surrogate potency marker for consistent quality check on cells manufactured and released for treating ischemic diseases. The levels of VEGF in the conditioned medium of the present cell composition/IMP (BM MSCs) at P5 cultures are tested in 13 production batches. On an average, the amount of VEGF present per million cells of the IMP ranges from 2-5 ng/million cells/72 hrs (FIG. 1) which shows that the MSCs of the IMP are of high quality. Human VEGF Quantikine ELISA Kit (R&D Systems, Minneapolis, Minn.) is used for the experiments according to the directions of the manufacturer.

Figure 2:
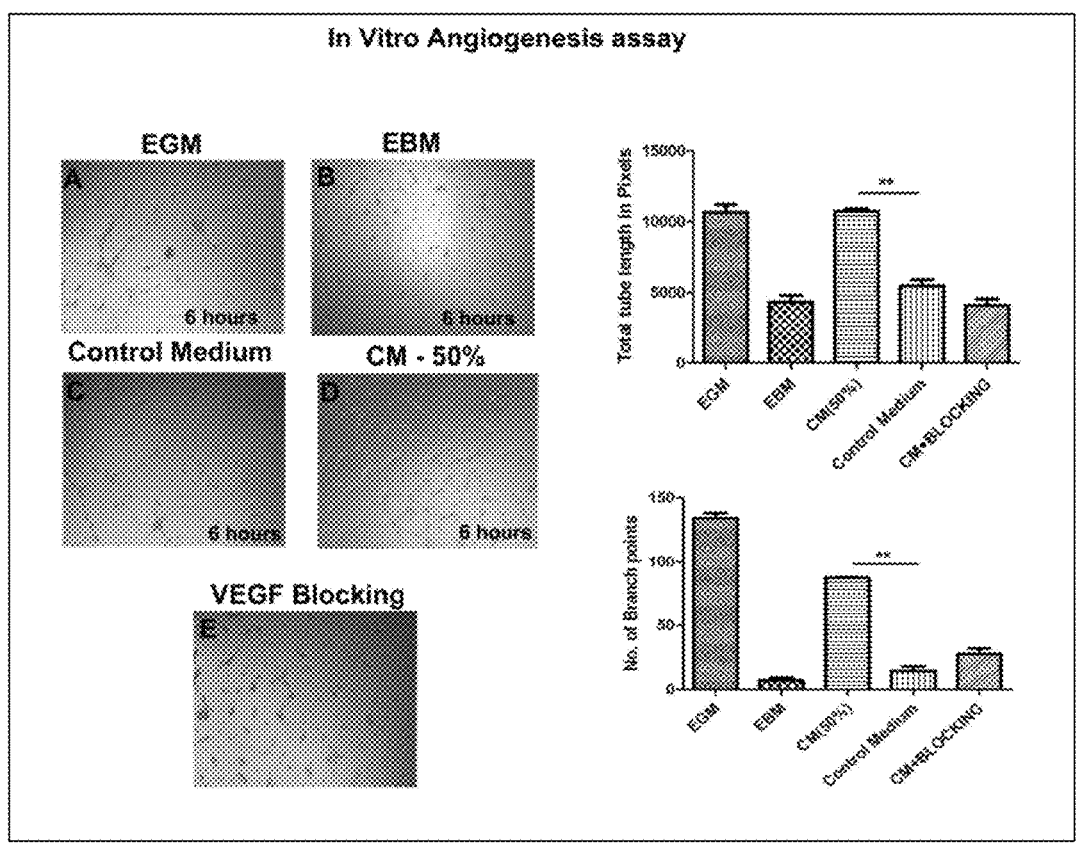
FIG. 2 depicts the results of in vitro angiogenesis assay evaluating the effect of MSC secreted paracrine factors in the process of angiogenesis.

(B) The ultimate requirement in vascular diseases is the reformation of blood vessels from pre-existing vasculature to recruit endothelial cells to migrate, proliferate and finally differentiate into capillary tubes at specific injury sites. To evaluate the effect of MSC secreted paracrine factors in the process of angiogenesis, an in vitro angiogenesis is performed on Human umbilical vein endothelial cells (HUVECs) wherein, the HUVECs are plated on GFR Matrigel in the presence of conditioned medium [CM] (50%), serum free medium (negative control) and EGM—Endothelial cell growth medium (Positive control). CM at 50% concentration itself is able to promote the tube formation within 6 hours of incubation. Neutralization of VEGF does not completely halt the tube formation but significantly reduces the tube length and average branch points. The results of this assay show that cell composition of the present disclosure facilitates new vessels formation thus showing the therapeutic efficacy of the composition (FIG. 2).

EXAMPLE 3

Comparison of Growth Factor Secretion Profile Between MSCs of Individual Donors and Pooled Compositions & their Effect in Management of Ischemic Conditions Since it is observed that there is considerable variation in the growth factor secretion profile of the individual in the growth (GF) array, a few growth factors are selected which are relevant for angiogenesis and quantified by ELISA for both the individual and pooled cells. The secretion profile of individual donors varies for each growth factor considerably except for TGF-β at both passage 3 and passage 5. On the other hand, consistent secretion of the factors is observed for the pooled cells for most of the growth factors tested. Concentration of the factors secreted by the pooled cells averages out compared to the individual donors except for Ang1 and TGF-β (FIG. 3).

Figure 3:
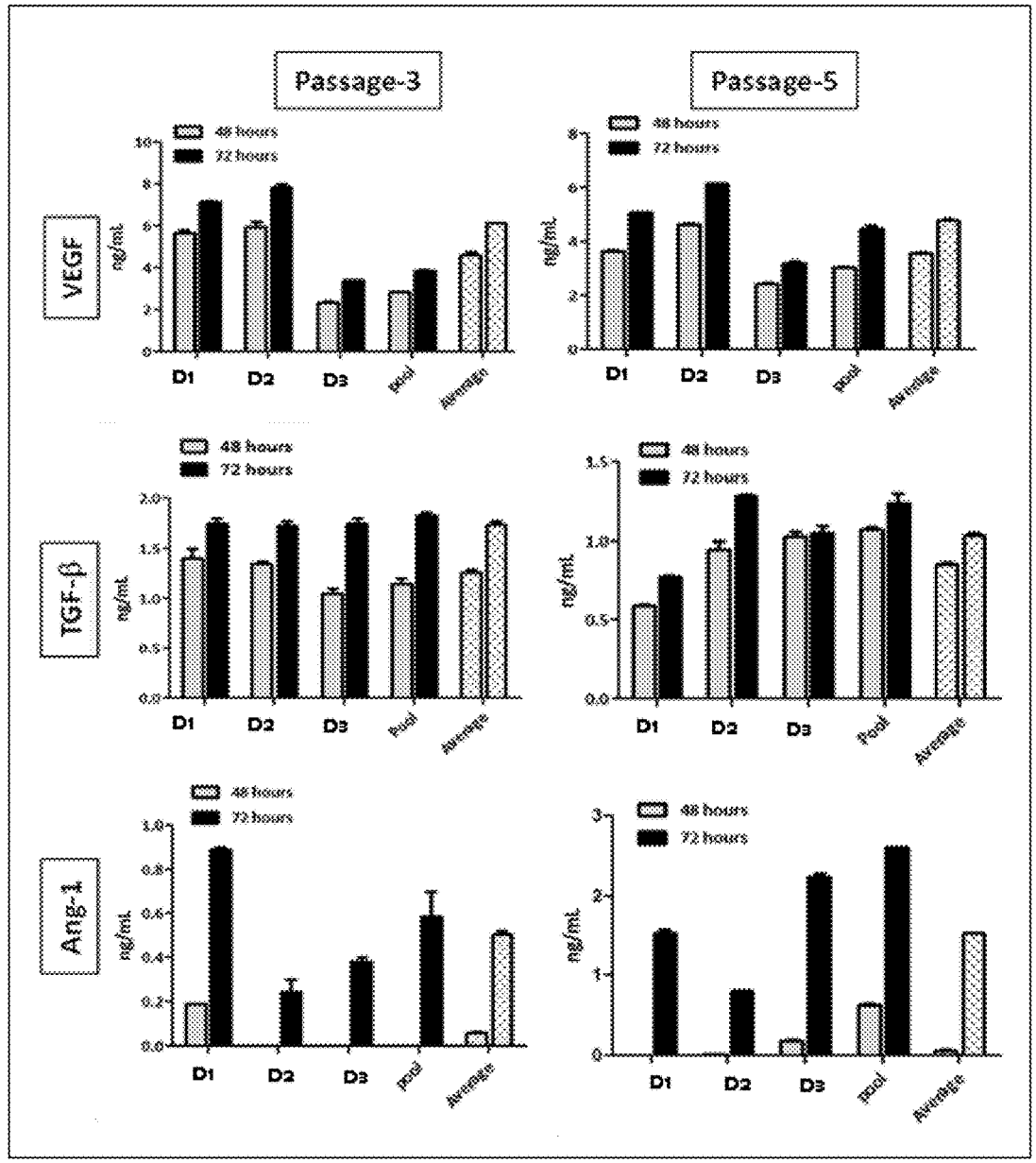
FIG. 3 depicts the angiogenic cytokine secretion profile of individual MSCs versus pooled MSCs measured by ELISA. The individual donor cells are represented as Donor 1 (D1), Donor 2 (D2), Donor 3 (D3), whereas the pooled cells are represented as 'pool' in the figure.

Both these factors i.e. Ang1 and TGF-β, play an important role in the vasculogenesis and the pooled MSCs secrete higher levels of these factors when compared to the individual donors as seen in FIG. 3. Further, it is known that basic cytokine prolife of the individual donors vary for some of the cytokines and not for all. The present cytokine/angiogenic data (FIG. 3) clearly establishes that pooling enhances the cytokine secretion profile and thus significantly increases the angiogenic ability of pooled MSC compositions for the management of ischemic conditions.

As per FIG. 3, a considerable variability in the secretion profile of the individual donors is observed. On the contrary, a minor variation is observed with the pooled cells. Further, pooled BM-MSCs produce consistent level of angiogenic factors such as VEGF, TGFb and Ang-1 at passage 5. Overall results obtained from quantifying the paracrine secretion clearly establishes that pooling of individual donors produces consistency in terms of angiogenic factors that are known to play an important role in angiogenesis and vasculogenesis, thus suggesting the improved efficacy of pooled and expanded allogeneic MSCs in the management of ischemic conditions.

Also, potential reasons for the inconsistent results in MSC clinical trials of individual MSCs is due to their variability in the secretion profile of various cytokines which are overcome by the pooling technology of the instant disclosure, and thereby enhancing the efficacy in the treatment if ischemia.

The Conditioned medium isolated/harvested from cell culture is rich in cell secretome comprising growth factors, cytokines, chemokines, small molecules and other factor. Thus, the conditioned medium collected during the harvest of stem cells can be used in the local administration of would/injury.

EXAMPLE 4

Figure 4:
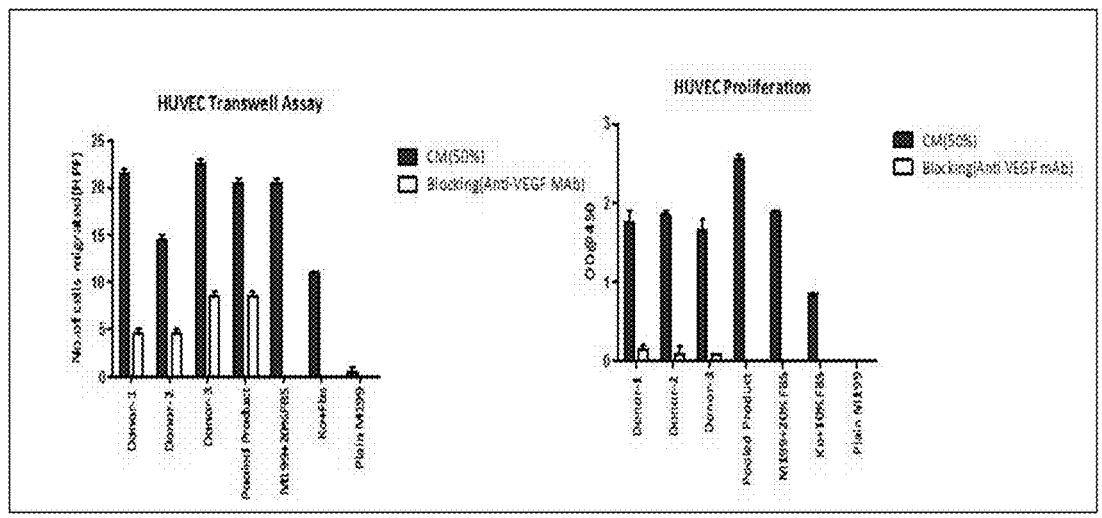
FIG. 4 depicts the in vitro functional angiogenesis data transwell migration and proliferation using HUVEC cell line.

Comparison of Angiogenic Ability of Conditioned Medium Derived from Individual MSCs and Pooled MSCs & their Significance in Management of Ischemic Conditions To further validate the cytokine profile results, in vitro functional angiogenesis assays are performed to compare the angiogenic ability of individual and pooled cells. Conditioned medium (CM) derived from the pooled cells promotes enhanced angiogenic activity compared to the individual donors by promoting HUVEC migration, proliferation and differentiation tubes on growth factor reduced matrigel as seen in FIG. 4. It can be inferred from FIG. 4 that the angiogenic marker expression in the conditioned medium derived from pooled cells are either superior or average of all the three donors (Donor-1, Donor-2 and Donor-3).

The above results prove that the conditioned medium derived from pooled MSCs show enhanced angiogenic activity and vasculogenesis when compared to conditioned medium derived from individual donor MSCs, thus showcasing the improved efficacy of pooled MSC derived conditioned medium for treatment of ischemic conditions, such as CLI from Buerger's disease and PAD, and ICM.

Further, the above results clearly indicate that the pooled cell composition of the present disclosure is more consistent and stable in terms of angiogenic marker expression when compared to the individual donors. This also indicates that there exists an individual to individual variability in the expression of angiogenic marker which would require multiple screening processes to select an individual with high expression. While pooling the cells as used in the instant disclosure reduces/minimizes individual variability to obtain a consistent and stable cell composition for the management of ischemia.

Moreover, the present example in combination with results of the Examples below establishing the efficacy of the pooled stem cell composition indicates the improved efficacy of combined employment of stem cell therapy (i.e. composition of the instant disclosure) and application of conditioned medium (i.e. employing pooled MSC derived conditioned medium) in the management of ischemic conditions.

Materials Used to Arrive at Examples 5 and 6 of the Present Disclosure

The materials used to perform the experiments (Examples 5 and 6) described in the instant disclosure are as follows—
Surgicals: Fine pointed forceps, pointed forceps, spring scissors, surgical scissors, needle holder, retractor, cautery tool; BD (1 ml) and Hamilton (100 & 250 µL) syringes ($27_{1/2}$ Gauge); sterile Phosphate Buffered Saline (PBS), sterile cotton plugs, sterile cotton swabs, sterile eppendrof tubes (1.5 mL, 2 mL), pipettes, filter paper, 70% Alcohol/Isopropyl alcohol, alcohol swabs, absorbable tissue paper, betadine and other essential items. The animal model used for the study is BALB/C Nude mice (Source—Harlan, UK, Registration No. 1089/c/07/CPCSEA dated 27/07/07). Further, the geographical origin of said BALB/C Nude mice is not India.

EXAMPLE 5

In-Vivo Evaluation of Therapeutic Potential of Pooled Mesenchymal Stromal Cells in Animal Model of Hind Limb Ischemia (LI)—(Pre-Clinical Study)

Experiments to evaluate efficacy and the effective therapeutic dosage of allogeneic and pooled human bone marrow derived Mesenchymal Stromal Cells (MSCs) in the treatment of CLI is carried out in an animal model of hind limb ischemia (LI). The animal model used is immunocompromised BALB/C nude mice.

Experimental Procedure
Induction of Hind LI in BALB/c Nude Mice

Animals are randomized based on the body weight before the start of experiment. Under isoflurane anesthesia (1-3% in 100% oxygen flow rate of 1 L/min), mice are placed in supine position over a heated pad on the operating table and hind limbs are extended and secured with a piece of tape. Then, the skin is wiped three times with alternating Betadine and alcohol swabs. A dissection microscope at 10× or 20× magnification is used for enlarged view of the hind limb region during the procedure. Using fine forceps and surgical scissors, a small incision (approximately 1 cm long) is made on the left leg, originating from the knee towards the medial thigh of the limb. Then using sterile cotton swabs moistened with saline, the subcutaneous fat tissue surrounding the thigh muscle is gently brushed away. Using retractor, the incised area is opened to obtain a better view of the lower extremity vasculature. Fine forceps and a fine pointed cotton swabs are used to gently pierce through the membranous femoral sheath to expose the neurovascular bundle. Then, using a clean set of fine forceps and cotton swabs, the femoral artery and vein are separated and dissected from the femoral nerve at the proximal location near the groin. After the dissection, for the first ligation 6-0 silk strand suture is passed underneath the proximal end of the femoral artery and vein, then the proximal femoral artery and vein are occluded using double knots. For the second ligation, a strand of 6-0 suture is passed underneath the distal end of the femoral artery and vein proximal to the popliteal artery. Occlusion of the proximal and distal femoral artery and vein with a second set of double knots just proximal to the first set of knots is also carried out for easy gripping of the artery during the transaction procedure. A segment of femoral artery and vein is thereafter transected between the distal and proximal knots with a fine pointed cotton swab and a pair of spring scissors. Then the retractor is removed and the incision area is closed using surgical clips. After the incision is closed, the animal is placed on top of a draped heated pad in the cage and monitored continuously until recovery. Postsurgical care is carried out according to Institutional Animal Ethics Committee guidelines.

Experimental Design and Treatment

Nineteen female athymic BALB/c Nude mice are housed in Individually Ventilated Cages (IVCs). Animals are divided into 3 groups. The dose level and route of administration is indicated in Table 1. Immediately after the ligation, each animal is injected with either 50 µL of PlasmaLyte-A (vehicle control) or BM-MSC composition [allogeneic and pooled human bone marrow derived Mesenchymal Stromal cells (MSC's, $2\times10^6$ and $5\times10^6$) along with vehicle/excipients] intramuscularly around the ligation site at five different places/sites i.e. Intra muscular injection around the femoral artery ligated area (approximately 10 µL at each site). All the animals are observed for a period of 28 days at regular intervals i.e., 0, 3, 7, 14, 21 & 28 days for any changes/reactions in the leg.

TABLE 1

Grouping and dosing of animals

| Sl. No | Groups | No. of Animals | Treatment | Cell dose per Animal (in 50 ul) Route: Intramuscular injection around the femoral artery ligated area |
|---|---|---|---|---|
| G1 | Limb Ischemia + Vehicle | 5 | Vehicle (PlasmaLyte-A) | NA |
| G2 | Limb Ischemia + BM-MSCs | 7 | BM-MSCs | $2 \times 10^6$ |
| G3 | Limb Ischemia + BM-MSCs | 7 | BM-MSCs | $5 \times 10^6$ |

Note:
NA—Not Applicable

Observations & Results

Statistics: All data are presented as mean±SEM in this section. For parametric analysis, ANOVA followed by Dunnett's test, and for nonparametric analysis, Kruskal-Wallis test are carried out using Graphpad Prism5 software. 'P' values are presented at each table and figure. P<0.05 is considered as significant difference.

1. Body Weight

Cage side observations, body weight measurements are carried out on regular basis (0, 3, 7, 14, 21 & 28 days) for all mice groups during the study period. The results clearly shows that mean body weight of each group do not significantly change over time.

2. Morbidity & Mortality

All the animals are checked for morbidity and mortality during the study. During the experimental period, no treatment related morbidity/mortality is observed, which indicates that BM-MSCs at the tested doses are non-toxic under the test conditions.

3. Limb Necrotic Scoring and Photographs

Animals are observed individually for visible signs of limb necrosis on 0, 3, 7, 14, 21 and 28th day after HLI and are photographed. Scoring is performed as mentioned below—
0=no necrosis,
1=necrosis in one toe,
2=necrosis in two or more toes,
3=foot necrosis,
4=leg necrosis,
5=autoamputation of the entire leg.

Figure 6:
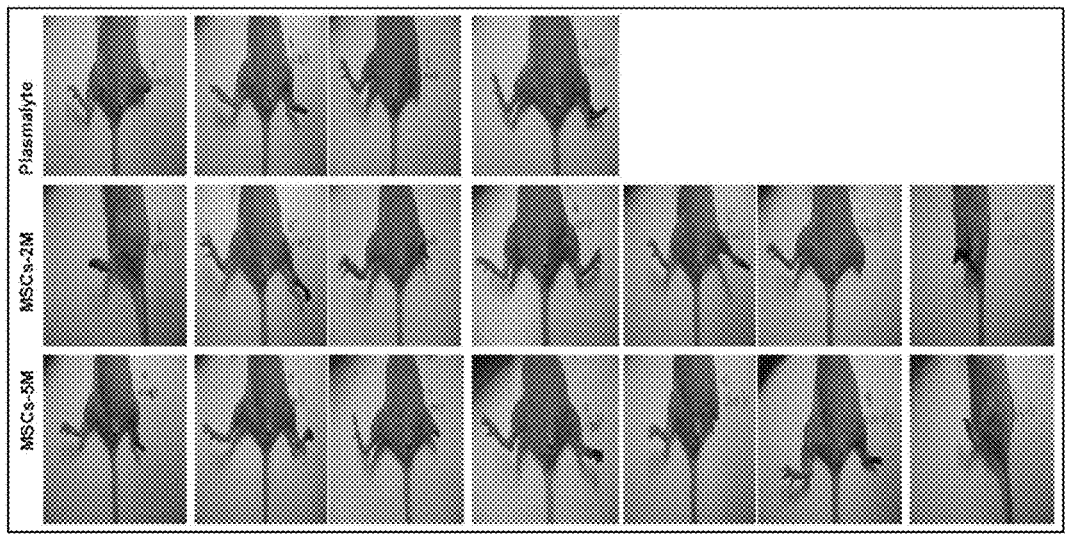
FIG. 6 depicts the photographs of LI animals treated with Plasmalyte (control) and BM-MSCs after 28 days.

Mean necrotic score is calculated for each group and compared between groups. The mean necrotic scores calculated on 0, 7, 14, 21 and 28 days after HLI (hind limb ischemia) clearly show that, while in the Plasmalyte-A treated group all animals developed foot necrosis, however, 28.57% and 42.87% of the animals showed resistance to the development of necrosis in the 2 & 5 million BM-MSC composition treated groups respectively (FIG. 6).

4. Histological Analysis

Animals are euthanized at the end of the study (28th day after LI) according to IAEC (Institutional Animal Ethics Committee) protocols. Adductor and soleus muscles tissues are collected and immediately fixed in 10% neutral buffered formalin. Five micron histology sections are stained with hematoxylin (H) and eosin (E). Using Leica DFC 425 software, representative photographs are taken with a Nikon digital camera (Nicon Eclipse 80i). Histopathological observations such as degeneration, inflammation and muscle necrosis are carried out from five separate fields in four distinct areas in each specimen. Total numbers of each incidents of degeneration, inflammation and muscle necrosis are calculated from each group. In animals which had autoamputation, the soleus muscles are not collected and in such cases, the maximum histological scoring of 5 (severe) is given for the degeneration, inflammation and muscle necrosis.

Figure 7:
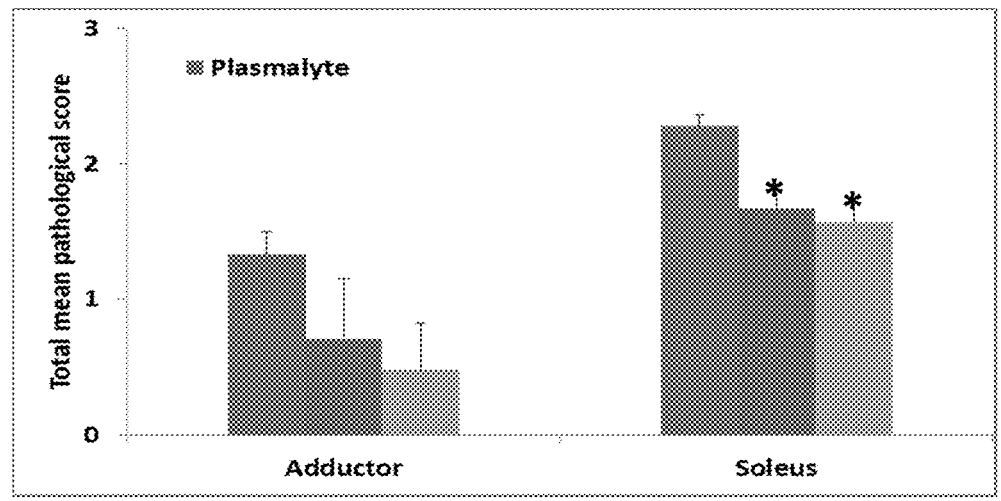
FIG. 7 depicts the total mean pathological score of adductor and soleus muscle of LI animals treated with either Plasmalyte A or BM-MSCs. Values are expressed as Mean±SEM. **$P<0.01$ compared to total mean pathological score in soleus muscle of Plasmalyte A treated mice.
Figure 8:
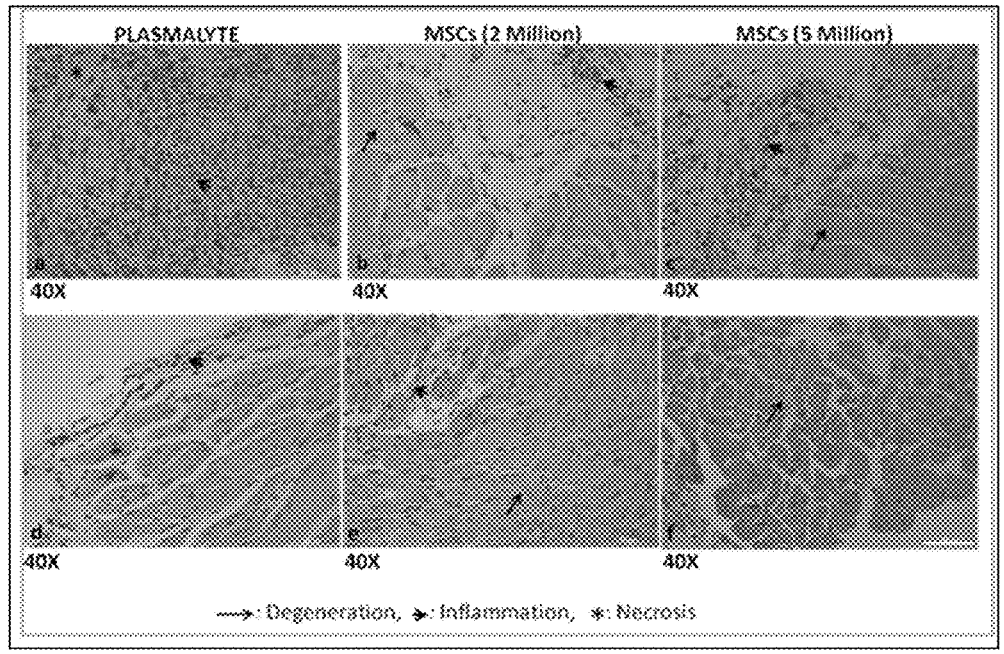
FIG. 8 depicts the images of hematoxylin and eosin (H&E) stained adductor (a-c) and soleus (d-f) muscles of LI mice treated with Plasmalyte and BM-MSCs (magnification at 40×). Scale bar shows the 50 µm.

As described above, adductor and soleus muscles are collected from each group and subjected to histopathological scoring of degeneration, inflammation & necrosis to understand treatment response to LI. The total mean pathological score is significantly decreased (i.e. P<0.01) in soleus muscle of BM-MSCs treated animals but not in adductor muscle (FIG. 7) when compared with plasmalyte treated group. The autoamputation animal's soleus muscles are not available as explained above and hence only the calculation of fiber area from the soleus muscle collected animals is performed. Histological examination of hematoxylin & eosin stained adductor (FIG. 8, a-c) and soleus muscle (FIG. 8, d-f) from PlasmaLyte-A treated mice reveal extensive muscle necrosis and degeneration with infiltration of numerous granulocytes and neutrophils compared to BM-MSCs treated mice. In contrast, BM-MSCs treated mice demonstrate reduced muscle degeneration compared to the PlasmaLyte-A treated mice. The total mean pathological score is significantly decreased (p<0.01) in soleus muscle of BM-MSCs treated animals than adductor. Representative images of the adductor and soleus muscle are presented in FIG. 8.

To summarize, LI model is developed in BALB/c nude mice by femoral artery and vein ligation. This model is used for studying therapeutic potential of human bone marrow derived pooled, expanded and allogeneic Mesenchymal Stromal Cells (BM-MSCs) composition. BM-MSC compositions are administered via. IM route as a single dose at multiple sites, immediately after the surgery. The animals are monitored for 28 days. While in the PlasmaLyte-A treated LI group, all animals are shown to develop foot necrosis, about 28.57% and 42.87% animals show protection in the 2 & 5 million BM-MSCs treated group respectively. Furthermore, 50% animals also show limb necrosis and autoamputation in plasmalyte treated LI group which indicates that the vehicle PlasmaLyte-A do not have any protective effect on the progression of ischemia. In animals which are treated with 2 million BM-MSCs, 71.43% animals show foot necrosis and 28.57% animals had limb necrosis. Lastly, in animals treated with 5 million BM-MSC's, there is 57.14% foot and 28.57% limb necrosis. Further, from the histology results, it is observed that the total mean pathological score is significantly decreased in soleus muscle of BM-MSC treated animals but not in the adductor muscle when compared with PlasmaLyte-A treatment. These results clearly conclude the improved efficacy of the present pooled and expanded allogeneic BM-MSC compositions in the treatment of limb ischemia.

EXAMPLE 6

Evaluation of the Efficacy of Human Bone Marrow Derived Pooled and Expanded Mesenchymal Stromal Cells (BM-MSCs/Stempeucel®) in a Murine Model of Hind Limb Ischemia Based on the preliminary clinical study results (EXAMPLE 5), a second study is performed in BALB/c Nude mice to confirm the efficacy of Stempeucel®/the instant composition using the unilateral hind limb ischemic model.

Experimental Procedure

Figure 9:
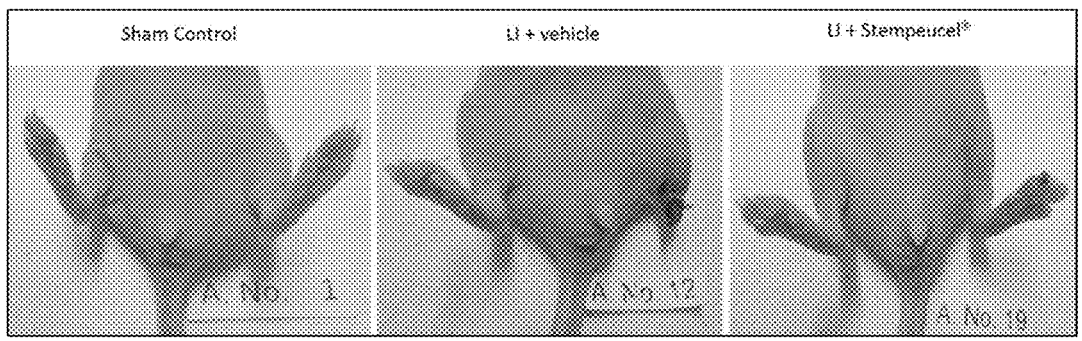
FIG. 9 depicts the representative photographs of sham control, LI+vehicle control, LI+Stempeucel®/instant composition treated animals at day 28.

Female BALB/c nude mice (obtained from Harlan, UK), aged between 10 and 12 weeks are used to establish the hind limb ischemia model. After randomization (Table 2 below), under isoflurane anaesthesia (1-3% in 100% oxygen flow rate of 1 L/min) the left femoral artery is separated from the femoral bundle after the skin incision. Extended femoral ligation is performed using 6-0 silk sutures. In the sham/control group, animal skin is incised and immediately closed without femoral ligation. A stereo microscope is used to perform the above surgical procedure (FIG. 9).

After the surgical procedure, the control animals are injected intramuscularly with 50 µl of Plasmalyte A and the test animals are injected intramuscularly around the femoral artery ligated area with 50 µl of Stempeucel® at the dose of $5 \times 10^6$ cells suspended in a volume of 50 µl Plasmalyte A (vehicle/carrier) around the ligation area at five different sites (approximately 10 µl injected at each site). The test item is administered 2 hours after the surgery, as this would allow the animal to recover from anesthesia and surgical trauma.

TABLE 2

Grouping and dosing of animals

| Sl. No | Groups | No of Animals | Treatment | Cell dose/Animal (in 50 ul) Route: Intramuscular |
|---|---|---|---|---|
| G1 | Sham Control | 3 | Vehicle | NA |
| G2 | Limb Ischemia + Vehicle | 10 | Vehicle | NA |
| G3 | Limb Ischemia + stempeucel ® | 10 | stempeucel ® | $5 \times 10^6$ |

Note:
NA—Not applicable

Observations: All the animals are monitored for 28 days for morbidity, mortality and clinical signs. Animals are assessed for visible signs of limb necrosis ambulatory and functional abnormalities at day 0, 1, 3, 7, 14, 21 & 28 after limb ischemia. The blood flow measurement of both ischemia induced and normal limb is performed at day 28 using laser Doppler imaging system (LDI2, Moor Instruments, UK). The blood flow measurements are expressed as a ratio of the flow in the ischemic limb vs. normal limb.

On day 28, all the animals are sacrificed using excessive isoflurane anesthesia. Complete necropsy and macroscopic examination is performed for all treated and control animals. For efficacy assessment and local injection site reaction, muscles like adductor, soleus, gastrocnemius and semimembranosus/gracilus are collected, weighed and processed from all the animals for histological analysis [preserved in 10% neutral buffered formalin (NBF)]. Samples from following tissues and organs are collected, weighed and is fixed in 10% neutrally buffered formalin (NBF): brain; lungs; heart; liver; pancreas; spleen; stomach; small intestine; kidneys; femoral bone; ovary; lymph nodes and site of injection. The tissues are processed and stained with hematoxylin and eosin (H&E) for histology analysis.

Histological analysis is performed on the muscle section, (adductor, soleus, gastrocnemius and semimembranosus/gracilus) stained with H&E. The stained muscle sections are scored for muscle degeneration, inflammation and muscle necrosis from five separate fields in four distinct areas. Total numbers of each incident of degeneration, inflammation and necrosis is calculated from each group. In animals which had auto amputation, the muscles are not collected and in such cases the maximum histological scoring of 5 (severe) is given for the degeneration, inflammation and muscle necrosis. Muscle fiber area is quantified using Leica Queen Software.

Immunohistochemistry is performed in adductor, gastrocnemius and semimembranosus muscle section for human and mouse CD31, human VEGF and HNA. To measure capillary density, positively stained mouse CD31 capillaries and small arterioles are determined using bright field microscopy at 40× magnification. The capillary density is quantified using Leica Queen Software to count positively stained capillaries in five different fields per slides by a blinded observer.

Statistics: The results are represented as Mean±SEM. All the groups are compared by one-way ANOVA followed by Dunnett's multiple comparisons using graph pad prism5 software. $p<0.05$ is considered as a significant change. To calculate the degree of freedom chi square test is also performed.

Results and Discussion:

Mortality and Morbidity: During the experimental period, there is no Stempeucel®/BM-MSC cell composition treatment related morbidity or mortality, which indicates that Stempeucel®/BM-MSc cell composition at the tested dose is nontoxic under this test condition. There are no abnormal local reactions at the site of Stempeucel® injection and no abnormal clinical signs are observed throughout study period.

Scoring and photographs: Animals are observed individually for visible signs of limb necrosis on 0, 3, 7, 14, 21 and 28th day after hind limb ischemia (HLI) and are photographed. Scoring is performed as mentioned below:

TABLE 3

Necrotic Scoring-Limb necrosis scores

| Score | Description |
|---|---|
| 0 | No necrosis |
| 1 | One toe necrosis |
| 2 | Two or more toes necrosis |
| 3 | Foot necrosis |
| 4 | Leg necrosis |
| 5 | Autoamputation of the entire leg |

TABLE 4

Ambulatory scoring

| Score | Description |
|---|---|
| 1 | Normal Function |
| 2 | Plantar function |
| 3 | Dragging of foot |

Figure 10:
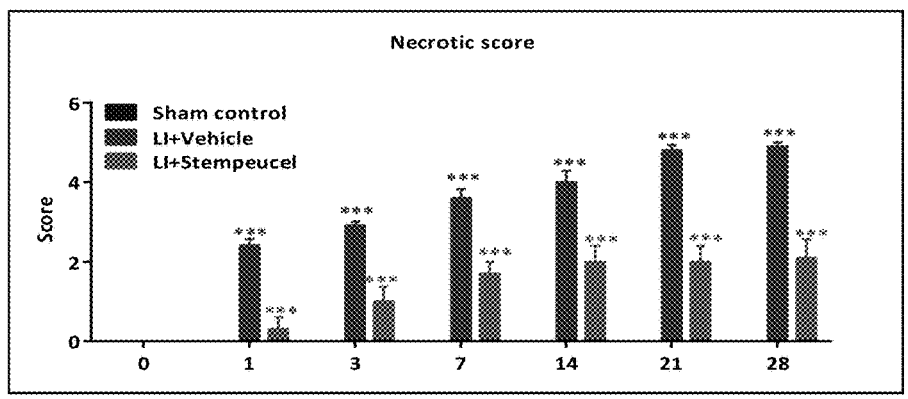
FIG. 10 depicts the mean necrotic score in sham control, LI+vehicle control, LI+Stempeucel® treated animals at different time points. Values are expressed as mean±SEM. ***$P<0.001$ compared to the LI+vehicle control.
Figure 11:
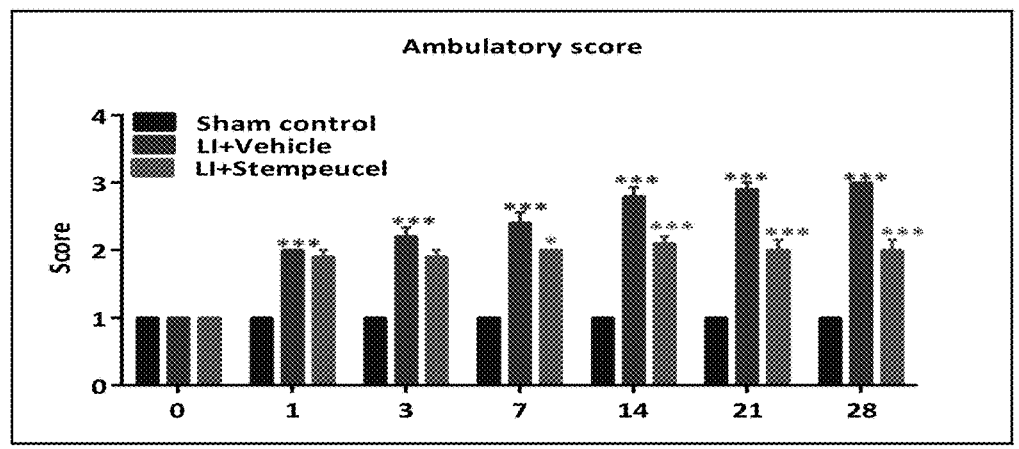
FIG. 11 depicts the mean ambulatory score in sham control, LI+vehicle control, LI+Stempeucel® treated animals at different time points. Values are expressed as mean±SEM. *$P<0.05$, ***$P<0.001$ compared to the LI+vehicle control.

In this study, Stempeucel® is administered intramuscularly around the femoral artery ligated area to demonstrate the improvement in limb function and reduction in ischemic damage and improvement in limb function. Significant improvement is observed in the cell treated group in terms of limb function (ambulatory score, $p<0.001$, see FIG. 11) and limb salvage (necrotic score, $p<0.05$ to 0.001, FIG. 10) as compared to the vehicle control.

TABLE 5

Table depicting Stempeucel ®/BM-MSCs composition administration preventing limb loss and necrosis in BALB/c nude mice

| Groups | Complete Limb Salvage[a] | Limb Salvage with one toe necrosis[b] | Limb Salvage with two or more toe necrosis[c] | Limb Salvage with foot necrosis[d] | Limb Salvage with Ankle necrosis[e] | Limb Loss[f] |
|---|---|---|---|---|---|---|
| Sham Control (n = 3) | 100% | 0 | 0 | 0 | 0 | 0 |
| LI + Vehicle (n = 10) | 0 | 0 | 0 | 0 | 10% | 90% |
| LI + stempeucel ® (n = 10) | 20% | 0 | 50% | 20% | 0 | 10% |

(Percentage amelioration of necrosis/limb salvage by intramuscular administration of stempeucel ®/BM-MSCs composition in a BALB/c nude mouse model of Hind Limb Ischemia:
[a]No necrosis,
[b]One toe necrosis,
[c]Two or more toe necrosis,
[d]Partial or complete foot necrosis,
[e]Necrosis in ankle and above,
[f]Auto-amputation of the entire leg).

Gross assessment of ischemic severity demonstrates that at 28 days after femoral ligation, spontaneous auto-amputation occurs in 9 out of 10 (90%) and one animal develops leg necrosis in the vehicle injected group. In contrast, Stempeucel®/pooled and expanded BM-MSCs composition injected animals clearly demonstrate complete limb salvage in 2 out of 10 (20%), limb salvage with only toe necrosis in 5 out of 10 (50%), limb salvage with foot necrosis 2 out of 10 (20%) and spontaneous auto-amputation is observed only in 1 out of 10 animals (10%) [Table 5]. Thus the results of this study validate the efficacy of the instant pooled and expanded allogeneic BM-MSC compositions in managing hind limb ischemia.

Figure 12:
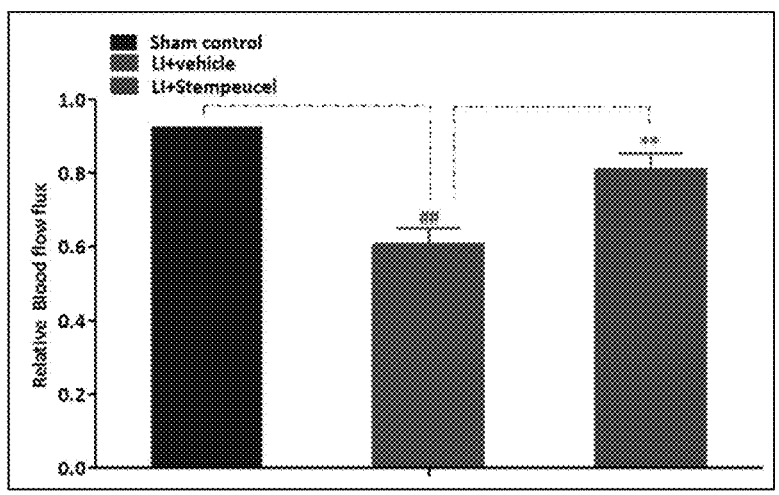
FIG. 12 depicts the Laser Doppler blood flow flux measured in sham control, LI+vehicle control and LI+Stempeucel® group animals at 28 day after LI. Values are expressed as Mean±SEM. ##$p<0.01$, sham control Vs LI Vehicle.**$p<0.01$ LI vehicle Vs LI+Stempeucel® treated animals.

Measurement of Hind Limb Blood Flow: Laser Doppler measurements at day 28 show a significant improvement in the blood flow (p<0.01) of the hind limb ischemic animals treated with Stempeucel®/pooled and expanded allogeneic BM-MSCs/instant composition as compared to the vehicle treated animals (FIG. 12). The recovery of blood flow in the Stempeucel®/instant composition administered animals is correlated with increased capillary density which suggests that the mechanism of action of Stempeucel®/instant composition is through increased angiogenesis and arteriogenesis. All the above data clearly demonstrates the efficacy of Stempeucel® in an animal model of hind limb ischemia.

Toxicological Assessment: Intramuscular administration of Stempeucel®/instant composition at the dose levels of 5×10⁶/animal does not reveal any gross and histological changes in all the organs examined.

Figure 13:
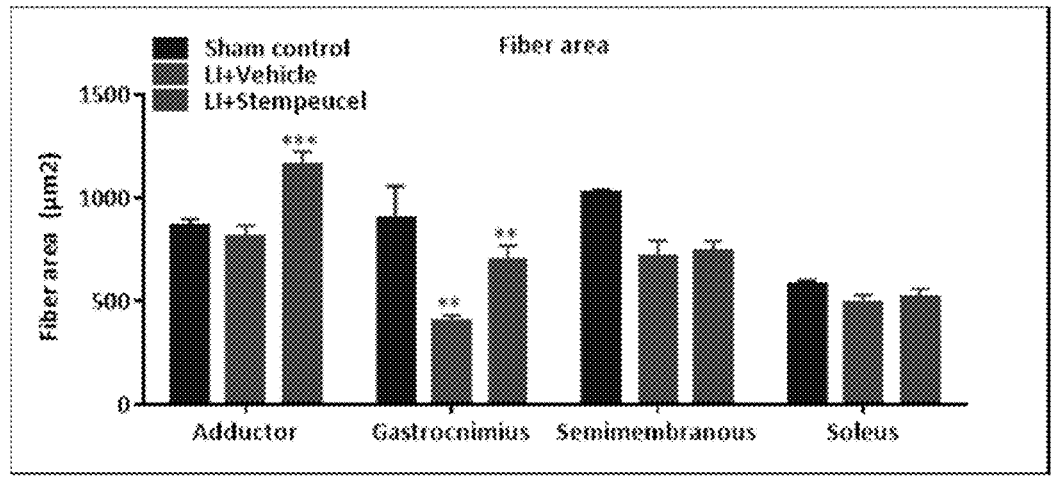
FIG. 13 depicts the muscle fiber area of sham control, LI+vehicle control and LI+Stempeucel® treated animals at 28 day after LI. Values are expressed as Mean±SEM. ##$P<0.01$, Sham control Vs LI Vehicle, $P<0.01$ and *$P<0.001$, LI vehicle Vs LI+Stempeucel®.

Efficacy Assessment: Histological analysis of limb muscles at day 28 after cell injection reveals that Stempeucel®/instant composition treatment significantly increases the total muscle fiber area in gastrocnemius and adductor muscle compared to the vehicle control (FIG. 13). The muscle degeneration, inflammation and muscle necrosis are also scored. The results demonstrate that Stempeucel®/instant composition treatment significantly reduces muscle necrosis, degeneration and inflammation when compared with vehicle control group (FIG. 14).

Immunohistochemical Analysis: Immunohistochemical staining of the muscle tissues obtained from various groups of animals with anti-human nuclear antigen specific antibody shows that human BM-MSCs are detectable on day 28 around the injected areas (FIG. 15). Mouse CD31 specific staining is observed in the adductor, gastrocnemius and semimembranosus muscles of the majority of animals injected with BM-MSCs. In fact, counting of mouse CD31+ve cells in these animals reveals significant increase in capillary density (FIG. 16) and arteriogenesis in all three muscles types in comparison to the vehicle administered animals (p<0.01). Immunohistochemical staining performed on these tissues with anti-human VEGF and anti-human CD31 antibodies also show some positivity, however, the staining is very sparsely distributed. These results showcase the improved stay (as high as 28 days) of the instant pooled and expanded allogeneic MSC composition at the ischemic site.

Further, these results suggest that the likely mechanism of action of Stempeucel®/instant composition is primarily mediated through paracrine secretion of various pro-angiogenic factors which aids in managing the ischemic conditions, in this case, the hind limb ischemia.

EXAMPLE 7

Biodistribution Study of the Pooled and Expanded MSC Composition of the Instant Disclosure A bio distribution study is conducted to demonstrate kinetics of 1,1'-dioctadecyl-3,3,3'3'-tetramethylindocarbocyanine perchlorate (CM-DiL) labelled allogeneic, pooled and expanded MSC composition/Stempeucel® tissue distribution after intramuscular administration in normal and diseased (Hind limb ischemia) BALB/c nude mice.

CM-DiL labelled Stempeucel (5×10⁶ cells) is injected intramuscularly at five different sites i.e. around the calf muscle area (specifically where the femoral artery ligation is done) both in hind limb ischemia (HLI) induced and normal BALB/c nude mice (sham BALB/c nude mice) and imaging is performed at different time points. The bio-distribution intensity data analysis reveals that the signal intensity peaked at day 1 in sham animals (control animals) and day 6 in LI animals. Thereafter, the signal intensities declined progressively in both groups. At day 28, there are no signals detected in sham animals treated with labelled cells, however, some signal is still detected in the ischemic animals (FIGS. 17 A & B).

The mean percentage of signal intensity in the ischemic animals is 12% at day 28 compared to the highest level observed on day 6. Sham control animals treated with Stempeucel®/instant composition show peak intensity of signals at day 1, whereas Limb Ischemia (LI) animals treated with Stempeucel® show peak intensity of signal on day 6. Stempeucel®/instant composition signal intensity in the sham control animals drastically reduces from day 3 and virtually disappears by day 21. In contrast, the signal is still detected in the ischemic animals up to day 28 (12%, 0.67±0.31×107 Photons/sec/mm$^2$ compared to day 6).

In conclusion, the bio-distribution pattern shows that the intramuscular injection of Stempeucel®/instant composition persists only at the injection site for the study duration of 28 days and does not get distributed to other organs. Therefore, the administration method/route of the instant disclosure is highly specific to the injury site and does not spread to other non-target sites of the body. Bio-distribution pattern of the Stempeucel®/instant composition also shows that intramuscular injection of Stempeucel®/instant composition predominantly localizes at the injection site and is not distributed to other organs although the kinetics of their distribution varies to a certain extent between the sham control and the ischemic animals.

EXAMPLE 8

Clinical Evaluation of Therapeutic Potential of Pooled Mesenchymal Stromal Cells in Humans with Critical Limb Ischemia (CLI)—Phase I Clinical Trial A randomized, double blinded, multicentric, placebo controlled, single dose study to assess the efficacy of bone marrow derived and ex-vivo cultured adult allogeneic and pooled mesenchymal stromal cell (MSC) composition is carried out wherein, said composition is administered intramuscularly via. calf muscle (FIG. 29) in human patients with critical limb ischemia (CLI) arising from Peripheral Arterial Disease (PAD). This study is conducted is in accordance to "Guidelines for Stem Cell Research and Therapy" by Department of Biotechnology and Indian Council of Medical Research (ICMR), 2007. Further, necessary approvals were taken from relevant ethics committees and Drug Controller General of India (DCGI) before starting the study.

Dosage: The MSC composition used for this study comprises pooled MSCs along with PlasmaLyte A, human serum albumin and DMSO. As mentioned in the above description, the MSC composition of the present disclosure is also referred as investigational medicinal product (IMP) or Investigational products. Further, 1-5 million MSCs per kg body weight is selected for dosing in humans. Specifically, in the present example, 2 million MSCs per kg body weight is taken.

Patient Screening: Human patients with clinical diagnosis of CLI as per Rutherford classifications for PAOD (Peripheral Arterial Occlusive Disorder) are screened at 4 centers in India and are enrolled in this study based on fulfilment of inclusion/exclusion criteria. Examinations at screening include specific assessment of ankle pressure and ankle brachial pressure index (ABPI). Post screening, the patients are randomly allocated to two arms namely; stem cell therapy arm and placebo arm. Most of these patients with CLI selected for the trial are "No Option" or "Poor Options" for Revascularization.

Treatment/BM-MSC Group and Placebo Group:

A total of 28 patients are screened for enrollment for the trial, of which 20 subjects are included in the study, 10 patients each in the BM-MSC arm and placebo group respectively. All twenty patients in each of the cohorts met identical inclusion and exclusion criteria. Block randomization is conducted in a centralized manner and communicated to the Investigational Medical Product Management Team. Subjects are randomly assigned in a double-blind fashion to each group in a 1:1 ratio of BM-MSC arm to placebo.

The investigational product (IP) i.e. pooled MSC composition is administered to the patients under stem cell therapy arm within 2±1 days of randomization The patients assigned to stem cell therapy arm receive a single intramuscular (IM) dose of bone marrow derived pooled and expanded allogeneic MSCs suspended in Plasma-Lyte A, 0.5 mL of cell suspension/kg body weight, injected at 40-60 multiple sites of the calf muscle of the ischemic limb, whereas patients assigned to the control arm receive a single IM dose of Plasma-Lyte A 0.5 mL/kg body weight, injected at 40-60 multiple sites of the calf muscle of the ischemic limb. Since the migratory capacity of stem cells is dependent on natural growth factors such as vascular endothelial growth factor which is highly unregulated in the hypoxic tissue, IM route of administration is selected so as to facilitate the MSCs in homing to the target site.

TABLE 6

Various treatment arms, drug, dosage and administration

| TREATMENT ARM | NAME OF THE DRUG | DOSING REGIMEN |
| --- | --- | --- |
| Stem Cell Therapy | Bone marrow derived and Ex vivo cultured adult allogeneic and pooled MSCs | Single intramuscular (IM) injection of MSCs (2 million cells per kg body weight) at 40-60 multiple sites of the calf muscle of ischemic limb |
| Placebo | Plasma-Lyte A | Single IM injection of Plasma-Lyte A at 40-60 multiple sites of the calf muscle of ischemic limb |

Note: As indicated in the above table, a total of 40-60 IM injections in the calf muscles at a dose of 2 million cells/kg body weight are given. This is approximately equal to 0.5 ml of cell suspension/kg body weight. For instance, if a patient's body weight is 50 kg, than a total of 100 million cells have to be injected which is equal to 25 ml of cell composition. This 25 ml of IMP is given as 40-60 injections in calf muscles wherein each injection volume is either 0.5 ml or 1 ml.

Patients are evaluated at 7 days (visit 3), 1 month (visit 4), 3 months (visit 5) and 6 months (visit 6) post IP administration for efficacy parameters.

Clinical Evaluation of the Study:

All clinical and laboratory data, for determining efficacy parameters are collected, and follow-up visits are performed at 1 day before and 7 days, 4 weeks, 12 weeks, 24 weeks after IMP/cell composition administration. The efficacy end points include—increase in ankle pressure and increase in ankle brachial pressure index (ABPI). Resting ABPI is measured by a Laser Doppler according to published protocol.

All data are recorded on manual case record forms (CRF) and verified by comparison with source documentation by third-party medical monitors.

Statistical Methods:

The SAS® package (SAS® Institute Inc., USA, Version 9.2) is used for statistical evaluation. All data are presented as mean±SD. For ABPI, change from baseline to 6 months is analyzed using an analysis of variance (ANOVA) model with factors for baseline, treatment and also compared between the two arms using Kruskal Wallis test. Statistical significance is defined as a two-sided p-value <0.05.

Results:

The results of ankle pressure and ankle brachial pressure index (ABPI) are recorded to evaluate the efficacy of the present pooled and expanded allogeneic MSC compositions.

Procedural safety: No infection, bleeding, or other complications related to the microbiological condition of the cells are detected in any patient after administration of BM-MSC/placebo as it is well tolerated. There are no other procedural related complications like allergic reactions or local swelling because of intramuscular injection of the IMP/cell composition establishing that the allogeneic pooled BM-MSCs are safe to inject into the CLI patients.

To further evaluate the safety aspect with respect to immunological profile, hematological, biochemical and urine analysis results from patients in both treatment arms are compared. The results are comparable at baseline and subsequent visits. Immunological profile (IFN-gamma, IL-1 & TNF-alpha levels) and lymphocyte profile (CD4, CD8 & CD25) are performed at one month, three months and six months after administration of IMP/cell composition or placebo, which reveal that it is comparable in both the arms (FIGS. 19-23, Tables 7 and 8). No significant difference in the blood lymphocyte profile or in the serum cytokine level is observed between BM-MSC and placebo administered patients establishing that the administered allogeneic cells did not elicit T-cells proliferative response in vivo, as estimated for the values obtained for the various subsets of T lymphocytes (Table 8). With respect to the levels of the pro-inflammatory cytokines it is observed that a difference exists between the BM-MSC administered patients and the placebo control patients at baseline, 1 month & 6 months after treatment, but they are either comparable with the baseline values or are within the normal range of these cytokines (Table 7). Collectively, these data confirms that the pooled and expanded allogeneic BM-MSC administration in CLI patients do not adversely alter the immunological profile.

TABLE 7

Summary of serum Cytokines values at screening, 1 month & 6 month follow-up after BM-MSC implantation

| Test | Screening | | 1 Month | | 6 Month | | Normal range (pg/ml) |
| --- | --- | --- | --- | --- | --- | --- | --- |
| | BM-MSC arm N = 10 Mean (SD) | Placebo N = 10 Mean (SD) | BM-MSC arm N = 9 Mean (SD) | Placebo N = 10 Mean (SD) | BM-MSC arm N = 7 Mean (SD) | Placebo N = 10 Mean (SD) | |
| Gamma - Interferon (pg/ml) | 24.4 (13.35) | 23.1 (24.07) | 37.8 (34.35) | 20 (24.67) | 9.1 (6.34) | 6.6 (3.57) | 0.01-168 |
| Interleukin 1 (pg/ml) | 22.6 (14.73) | 22.9 (15.31) | 33.1 (23.59) | 22.9 (21.73) | 26.6 (29.28) | 10 (3.26) | 0-400 |
| Tumor Necrosis Factor - alpha (pg/ml) | 14.2 (9.16) | 13.8 (10.11) | 16.6 (6.16) | 15.7 (7.98) | 11.4 (11.65) | 4.4 (2.47) | 0-3.22 |

TABLE 8

Summary of lymphocyte profile values at screening, 1 month & 6 month follow-up after BM-MSC implantation

| Test | Screening | | 1 Month | | 6 Month | |
| --- | --- | --- | --- | --- | --- | --- |
| | BM-MSC arm N = 10 Mean (SD) | Placebo N = 10 Mean (SD) | BM-MSC arm N = 9 Mean (SD) | Placebo N = 10 Mean (SD) | BM-MSC arm N = 7 Mean (SD) | Placebo N = 10 Mean (SD) |
| CD4 (cells/μl) | 923.1 (217.52) | 856.3 (237.29) | 905.6 (134.37) | 922.4 (451.48) | 1020.9 (405.67) | 954.4 (164.49) |
| CD8 (cells/μl) | 682.5 (253.96) | 688.3 (420.36) | 664.2 (183.02) | 644.9 (396.27) | 786.3 (329.27) | 727.9 (312.25) |
| CD25 (cells/μl) | 21.3 (22.22) | 16.3 (10.92) | 21.7 (14.34) | 22.0 (20.66) | 30.3 (25.36) | 35.3 (28.04) |

ABPI & Ankle Pressure: ABPI and ankle pressure are significantly increased at 24 weeks after BM-MSC injection as compared to the values obtained at baseline (Tables 9 and 10). A mean change of 0.22 is observed in ABPI in BM-MSC arm while, there is no change in the placebo arm from baseline to 6 months (p=0.0018). A mean change of 18.96 mmHg is noticed in ankle pressure in the BM-MSC arm compared to 3.92 mmHg change from baseline in the placebo arm (p=0.047) [FIG. 18 (A)].

TABLE 9

Evaluation of Efficacy Parameters

| Parameter | BM-MSC Arm | | Placebo | | Difference | P value |
| --- | --- | --- | --- | --- | --- | --- |
| | Baseline | 6 months | Baseline | 6 months | | |
| ABPI Mean (SD) | 0.554 (0.26) | 0.768 (0.15) | 0.592 (0.23) | 0.596 (0.14) | −0.17 | 0.0018 |
| Ankle Pressure | 64.37 (19.9) | 83.33 (11.55) | 62.7 (16.15) | 68.62 (17.67) | 13.03 | 0.047 |

TABLE 10

Analysis of change from baseline in Ankle pressure of target limb

| Term | Visit | Treatment A | | | Treatment B | | | Change from Baseline | | | |
| --- | --- | --- | --- | --- | --- | --- | --- | --- | --- | --- | --- |
| | | N | Mean | SD | N | Mean | SD | LS Mean | LS Mean Difference | p-value* | p-value** |
| Dorsalis Pedis | Baseline | 2 | 47.000 | 29.70 | 5 | 44.000 | 13.56 | . | . | . | . |
| | Visit 6 | 1 | 38.000 | . | 3 | 61.333 | 12.06 | . | . | . | . |
| Posterior Tibial | Baseline | 7 | 69.857 | 13.53 | 7 | 68.143 | 16.54 | 17.638 | 6.47 | 0.6269 | 0.8880 |
| | Visit 6 | 8 | 80.625 | 12.85 | 9 | 75.778 | 30.68 | 11.167 | . | — | |

Treatment A: Ex vivo cultured adult allogenic MSCs
Treatment B: Plasmalyte-A (Placebo);
*Using ANOVA
**Using Kruskal-Wallis test;
N = Number of patients with non-missing values;
Source Listing: Source Listing: ABPI- by Peripheral Doppler In the present clinical study, CLI is determined by an ankle pressure of =70 mmHg along with that of ABPI of =0.6. Both these selection criteria parameters show significant improvement in patients included in the BM-MSC arm while this is not the case in patients treated with placebo (p<0.05) [FIG. 18(B)].

Conclusion:

BM-MSCs injected intramuscularly at the calf muscle at a dose of about 2 million cells/kg body weight show improved efficacy in treating CLI by angiogenesis leading to revascularization. In particular, efficacy parameters such as ABPI and ankle pressure show significant improvement when compared to placebo.

EXAMPLE 9

Clinical Evaluation of Therapeutic Potential of Pooled Mesenchymal Stromal Cells in Humans with Critical Limb Ischemia (CLI)—Phase II Clinical Trial A non-randomized, open label, multi-centric, dose ranging, phase II study is conducted for assessing the efficacy and safety of intramuscular administration via. combined calf muscle and local administration (FIG. 29 and FIG. 30) of ex-vivo cultured adult bone marrow derived allogeneic mesenchymal stem cells (Stempeucel®/instant composition) in patients with critical limb ischemia due to Buerger's disease.

Methodology: In phase II, non-randomized, open label, multicenter, four arm study to evaluate efficacy and safety of ex-vivo cultured adult bone marrow derived allogeneic MSCs is conducted as compared to control group (standard protocol of care (SPOC)) in the treatment of CLI due to Buerger's disease. The study population consists of patients of either sex, aged between 18-65 years with Buerger's disease as diagnosed by Shionoya criteria. Eleven centersin India participated in the trial. A total of 126 patients were to be initially enrolled into 4 study groups in a sequential manner to the dose group of 1 million cells/kg body weight (36 patients), 2 million cells/kg body weight (36 patients), 4 million cells/kg body weight (36 patients) and the SPOC group (18 patients). During the enrolment of patients in the 2 million cells/kg body weight, the principal investigators of this clinical trial provided a general feedback that the patients who were administered with 1 million cells/kg body weight and 2 million cells/kg body weight were showing improvement in both the primary efficacy end points of the trial. Hence, patients were not recruited in the 4 million cells/kg body weight dose group. This example presents the data analysis of 1 million cells/kg dose group (36 patients; referred as D1m in this example), 2 million cells/kg dose group (36 patients; referred as D2m in this example) and SPOC group (18 patients; referred as SPOC in this example).

TABLE 11

Reference of different groups in this study

| Reference | Dose group | Intervention |
|---|---|---|
| D1m | 1 million cells/kg dose group | Administered with 1 million cells/kg along with standard protocol of care |
| D2m | 2 million cells/kg dose group | Administered with 2 million cells/kg along with standard protocol of care |
| SPOC | Control group | Administered with standard protocol of care alone |

TABLE NO. 12

Test and reference product, dose and mode of administration with batch number

| Study Treatment | Treatment duration | Dosing regimen | No. of Patients |
|---|---|---|---|
| Ex-vivo cultured adult bone marrow derived pooled and allogeneic MSCs | Intramuscular (IM) injection of MSCs, (1 million cells or 2 million cells per kg body weight) at 40-60 multiple sites of the calf muscle of ischemic limb and 2 ml around the ulcer (local administration) | One time injection during Visit 2 | 72 |
| Control group | Standard Protocol of Care | Visit 2 | 18 |
| Total | | | 90 |

Duration of Treatment: The study patients were evaluated for efficacy and safety parameters over a period of 6 months.

Efficacy Results:

Primary Endpoints

1. Rest Pain Assessment: The rest pain of CLI is graded on a visual analog scale (VAS) comprising of a horizontal line which grades the pain from 0 ('No Pain') to 10 (Worst Pain'). At each visit, the patients are enquired about the severity of the pain on that day and are requested to place an "X" mark on the horizontal line in relation to the two extremes.

The rest pain assessment is performed at baseline, at one month (visit 4), 3 months (visit 5) and 6 months (visit 6) follow-up. Rest pain scores across all the treatment groups are comparable at the baseline. The baseline rest pain scores are 6.84 in the D1m group, 7.03 in the D2m group and 6.66 in the SPOC group.

Longitudinal analysis of rest pain assessment using generalized estimating equations (GEE) in modified intent to treat (mITT) population shows that there is a decrease in the rest pain scores by 0.53 units [Standard Error (SE)=0.11] across all groups together per month which is statistically significant (p=<0.0001). Compared to the SPOC group, D1m group has 0.23 unit (SE=0.13) reduction in the rest pain per month, which is approaching statistical significance (p=0.0815), Confidence Interval (CI)=(−0.48, 0.03). However, D2m group has 0.3 units (SE=0.13) reduction in the rest pain per month compared to SPOC group, which is statistically significant (p=0.0193), CI=(−0.55, −0.05). The FIG. 24 depicts the rest pain scores, having groups with SE Error Bars.

2. Ulcer Area: Assessment of ulceration in the target limb is performed using a device called Visitrak. It enables the measurement of wound dimensions (area, length, width and depth) and produces a visible record of the dimensions of wound. The digital tablet converts a line tracing into a true area measurement which is used to calculate the area change (absolute and percentage) from the last area measurement.

The ulcer area assessment is performed at baseline, at one month (visit 4), 3 months (visit 5) and 6 months (visit 6) follow-up. The mean baseline ulcer area is of 6.42 cm$^2$ size in the D1m group, 4.09 cm$^2$ in the D2m group and 1.78 cm$^2$ in the SPOC group. D1m and D2m groups have larger ulcers compared to SPOC group at baseline (see FIG. 25).

Longitudinal analysis of ulcer area using GEE in mITT population shows that overall there is a significant decrease in the ulcer size by 18% (SE=0.03) across all groups together per month (p-value=<0.0001).

As compared to SPOC group, D1m group has 2% (SE=0.06) decrease in ulcer size per month (p=0.6967) CI=(0.87, 1.10).

As compared to the SPOC group, D2m has 11% (SE=0.05) decrease in ulcer size per month (p=0.0253) which is statistically significant CI=(0.80, 0.99). Hence, the second primary endpoint, healing of ulcers is achieved in D1m and D2m dose group.

Summarizing the primary endpoints, it is apparent that both the primary endpoints i.e., relief of rest pain and reduction in ulcer area are met by 1 million and 2 million cells/kg body weight dose group (see FIG. 25).

Secondary Endpoints.

1. Total Walking Distance: Graded treadmill testing is performed to accurately assess meaningful changes in patients with CLI in the physiological status of the claudication at baseline and in response to therapy. After resting in supine position for 20 minutes, patient walks on a treadmill at 2 mph (3.2 km/h) up a 12% grade for 60 minutes or until forced to stop because of claudication or other restrictions.

The total walking distance assessment is performed at baseline, at one month (visit 4), 3 months (visit 5) and 6 months (visit 6) follow-up. Total walking distance across all the treatment groups is comparable at the baseline. The baseline total walking distance is 0.35 km in the D1m group, 0.24 km in the D2m group and 0.57 km in the SPOC group.

Longitudinal analysis of total walking distance assessment using GEE in mITT population shows that there is an increase in the total walking distance values by 1.04 times (SE=0.01) across all groups together per month which is statistically significant (p=<0.0001) (FIG. 26).

D1m group has 1.03 times (SE=0.01) higher total walking distance per month when compared to SPOC group, which is statistically significant (p=0.0231), CI=(1, 1.06).

D2m group has 1.03 times (SE=0.02) higher total walking distance per month compared to SPOC group, which is approaching statistical significance (p=0.0577), CI=(1, 1.07).

2. Ankle Brachial Pressure Index (ABPI): The arm and leg blood pressure measurements are determined with an appropriate sized blood pressure cuff and the doppler device. The systolic blood pressure is determined in both arms, and the ankle systolic blood pressure is determined for the right and left posterior tibial (PT) or anterior tibial (AT) artery of the target limb. The ABPI for each leg is determined by using the higher reading from the posterior tibial or anterior tibial artery (ankle pressure) and the higher of the two brachial readings (brachial pressure). ABPI is calculated as a ratio of ankle pressure to the brachial pressure.

The ABPI assessment is performed at baseline, at one month (visit 4), 3 months (visit 5) and 6 months (visit 6) follow-up. ABPI across all the treatment groups are comparable at the baseline. The baseline ABPI is 0.52 in the D1m group, 0.47 in the D2m group and 0.68 in the SPOC group (FIG. 27).

Longitudinal analysis of ABPI assessment using GEE in mITT population shows that:

D1m group had 0.02 unit (SE=0.01) increase in the ABPI per month when compared to SPOC group, which was statistically better though not significant (p=0.1329), CI=(−0.01, 0.05).

D2m group had 0.03 unit (SE=0.01) increase in the ABPI per month compared to SPOC group, which was statistically significant (p=0.0132), CI=(0.01, 0.06).

3. QOL total score: King's College VascuQOL questionnaire is used in this study to assess the quality of life which is specifically developed for patients with lower limb ischemia. It contains 25 questions, each one with 7 possible answers and each question scored from 1 to 7. The questions are grouped into 5 domains: activity items (physical activity), symptom items, pain items, emotional items (psychological well-being) and social items (social activity). Out of the 25 questions, activity item comprised of 8 questions (score range from 0 to 56), symptom item comprised of 4 questions (score range 0 to 28), pain item comprised of 4 questions (score range 0 to 28), emotional item comprised of 7 questions (score range 0 to 49) and social item comprises 2 questions (score range 0 to 14). Increase in the score is considered as improvement in the Quality of Life (QOL). The King's College VascuQOL assessment is performed at baseline, at one month (visit 4), 3 months (visit 5) and 6 months (visit 6) follow-up. The King's College VascuQOL total score across all the treatment groups are comparable at the baseline. The baseline QOL total score are 0.51 in the D1m group, 0.45 in the D2m group and 0.62 in the SPOC group.

Longitudinal analysis of QOL total score assessment using GEE in mITT population shows overall increasing pattern in the score by 0.06 units (SE=0.01) at each subsequent visits across all the groups which was statistically significant (p=<0.0001) (CI=0.04, 0.09) (FIG. 28).

As compared to SPOC group, D1m group had an increase in the QOL total score of 0.03 units (SE=0.02) per month which was approaching statistical significance (p=0.0675) (CI=0, 0.06).

As compared to SPOC group, D2m group had increase in the QOL total score of 0.02 units (SE=0.02) per month which was statistically better though not significant (p=0.1823) (CI=−0.01, 0.05).

TABLE 13

Summary of results of efficacy end points in phase II clinical trials in patients administered with 1 million and 2 million pooled and expanded allogeneic MSC compositions

| Parameters | Baseline | 6 months FW | 12 months FW |
|---|---|---|---|
| Ulcer area (cm$^2$) | 25 | 0 | 0 |
| Ulcer depth (cm) | 0.3 | 0 | 0 |
| Rest pain (cm) | 7 | 0 | 0 |
| ABPI | 0.6 | 0.75 | 0.75 |
| Tcpo2-foot | 36 | 08 | 40 |
| Pain free walking time | 5 min 47 s | 60 min | 60 min |
| Pain Free Walking Distance | 0.31 Km | 2.43 Km | 3.2 |
| Maximum Walking time | 20 min 43 s | 60 min | 60 min |
| Maximum Walking Distance | 1.1 Km | 2.43 Km | 3.2 |

4. Angiogenesis—collateral blood vessels by Magnetic resonance angiogram (MRA): Magnetic Resonance Angiography (MRA) of lower limbs performed in the study is a high resolution contrast enhanced 3D gradient echo volumetric breath-hold examination with surface coils, followed by bolus chase MRA with dedicated peripheral vascular coil.

MRA is evaluated at baseline and at visit 6 to assess angiogenesis in the collateral and parent blood vessels.

Out of 34 patients in the D1m group, MRA is available for review in 29 (85.29%) patients, out of 35 patients in D2m group, MRA is available for review in 27 (77.14%) patients and out of 17 patients in SPOC group, MRA is available for review in 16 (94.12%) patients. The MRA is not available for review in 5 (14.71%) patients in D1m group, 8 (22.86%) patients in D2m group and one (5.88%) patient in the SPOC group.

At visit 6, in the D1m group, out of the 29 (85.29%) patients in whom MRA is reviewed, MRA reports of 19 (65.52%) patients are assessable and reports of 10 (34.48%) patients are not assessable for collateral vessels. MRA reports of 6 (31.58%) patients which are assessable for collateral vessels showed improvement while 13 (68.42%) patient's MRA report had either decrease in number of collateral vessels (3 patients) or are of same status (10 patients).

In the D2m group, out of the 27 (77.14%) patients in whom MRA is reviewed, MRA reports of 20 (74.07%) patients are assessable and reports of 7 (25.93%) patients are not assessable for collateral vessels. MRA reports of 9 (45%) patients which are assessable for collateral vessels showed improvement while 11 (55%) patient's MRA reports has either a decrease in number of collateral vessels (one patients) or was of the same status (10 patients).

In the SPOC group, out of the 16 (94.12%) patients in whom MRA is reviewed, MRA reports of 12 (75%) patients are assessable and 4 (25%) patients are not assessable for collateral vessels. MRA reports of 4 (33.33%) patients which are assessable for collateral vessels showed improvement while 8 (66.67%) patient's MRA reports are of the same status.

5. Safety Results:

The safety tests conducted demonstrate that ex-vivo cultured adult allogeneic and pooled MSCs have a favourable safety profile when injected intramuscularly at calf muscle and locally at the site of ulcer in patients with critical limb ischemia due to Buerger's disease.

Conclusion: This non-randomized, controlled clinical trial demonstrates that a single intramuscular dose of ex-vivo cultured adult allogeneic and pooled MSCs is safe and highly efficacious in alleviating the symptoms of Critical Limb Ischemia (CLI) due to Buerger's disease. Stempeucel® or the instant composition injected intramuscularly in the calf muscle and locally around the non-healing ulcer result in reduction of rest pain and healing of ulcers in an accelerated fashion in both the treatment groups (1 million cells/kg body weight and 2 million cells/kg body weight dose groups).

Thus, the present disclosure provides for pooled MSC compositions with specific dosage ranges and modes of administration for management of ischemic conditions. In an important aspect of the disclosure, said pooled MSC compositions at specified dosages and route of administration are employed for managing Critical Limb Ischemia (CLI), a symptom of Buerger's disease as well as Peripheral Arterial Disease (PAD) in a subject in need thereof, and/or management of an ischemic condition—ischemic cardiomyopathy (ICM). In another important aspect, conditioned media comprising bioactive/angiogenic factors is optionally employed along with the present composition to enhance the efficacy of managing ischemic conditions.

We claim:

1. A method of treating ischemia in a subject having or suspected of having the ischemia, said method comprising acts of administering a composition comprising pooled and expanded allogeneic mesenchymal stromal cells at a dose ranging from about 0.5 million cells per kg of body weight of the subject to 5 million cells per kg of body weight of the subject, optionally along with pharmaceutically acceptable excipient to the subject, wherein the pooled allogeneic mesenchymal stromal cells are expanded from passage 3 (P3) to passage 5 (P5), and wherein said composition is administered intramuscularly via one or more injections in at least two locations, a first location, wherein the first location is at least one site selected from the group comprising calf muscle region, thigh region, at or along or in the course of a constricted vessel or any combination thereof, and a second location, wherein the second location is local administration at or around the site of an ulcer, gangrene, or wound.

2. The method as claimed in claim 1, wherein the dose of the mesenchymal stromal cells ranges from about 1 million cells per kg to 2 million cells per kg of body weight of the subject.

3. The method as claimed in claim 1, wherein the mesenchymal stromal cells are derived from a source selected from the group comprising bone marrow, adipose tissue, wharton's jelly, and dental pulp, or any combination thereof; wherein the mesenchymal stromal cells are obtained by ex-vivo cell culturing; wherein at least 80% mesenchymal stromal cells are positive for cell specific markers CD73, CD90, CD105, and CD166 cells, and less than 10% mesenchymal stromal cells are positive for markers CD34, CD45, CD133, CD14, CD19, and HLA-DR.

4. The method as claimed in claim 1, wherein the pooled allogeneic mesenchymal stromal cells induce neovascularization at the administered site.

5. The method as claimed in claim 1, wherein the pharmaceutically acceptable excipient is selected from the group comprising carrier, cyropreservant, serum, and pre-formulated ready to use cryopreservation mixture, or any combinations thereof; and wherein the carrier is Multiple Electrolyte Injection, Hank's balanced salt solution (HBBS), saline, Lactated Ringer's Injection; the cyropreservant is Dimethyl Sulfoxide (DMSO), the serum is human serum albumin (HSA), and the pre-formulated ready to use cryopreservation mixture is animal protein-free defined cryopreservation medium.

6. The method as claimed in claim 1, wherein the ischemia is limb ischemia, ischemic cardiomyopathy (ICM), ischemic stroke, ischemic ulcers, or any combinations thereof.

7. The method as claimed in claim 1, wherein the subject is mammal; and wherein the composition is administered as a single dose at multiple sites; and wherein the composition stays for a time-period of about 1 to 28 days at the site affected by the ischemia.

8. The method as claimed in claim 1, wherein the treatment is characterized by a parameter selected from the group comprising reduction in rest pain, healing of ulcer, healing of necrosis, healing of gangrene, healing of lesion, healing of wound, increase in ankle pressure, increase in ankle brachial pressure index (ABPI), increase in transcutaneous partial oxygen pressure (TcPO2), increase in vasculogenesis, or any combinations thereof.

9. The method as claimed in claim 1, wherein the composition is formulated as an aqueous suspension.

10. The method as claimed in claim 3, wherein the mesenchymal stromal cells are derived from bone marrow.

11. The method as claimed in claim 6, wherein the limb ischemia is critical limb ischemia (CLI).

12. The method as claimed in claim 11, wherein the CLI is a result of Buerger's disease, peripheral artery disease (PAD), or a combination thereof.

13. The method as claimed in claim 7, wherein the mammal is human.

14. A method of treating ischemia in a subject having or suspected of having the ischemia, said method comprising acts of administering a composition comprising pooled and expanded allogeneic mesenchymal stromal cells at a dose ranging from about 0.5 million cells per kg of body weight of the subject to 5 million cells per kg of body weight of the subject, optionally along with pharmaceutically acceptable excipient to the subject, wherein said composition is administered intramuscularly through a combination of at least two sites selected from the group comprising calf muscle region, thigh region, at or along or in the course of a constricted vessel, locally at or near a site affected by the ischemia and local administration at or around the site of an ulcer, gangrene, or wound; and topical administration of a conditioned medium to the site affected by the ischemia, and wherein said administration of the conditioned medium is carried out either simultaneously or sequentially with the administration of the composition; wherein the conditioned medium is derived from the pooled and expanded allogeneic mesenchymal stromal cells.

15. The method as claimed in claim 14, wherein the conditioned medium is formulated as a formulation selected from the group comprising aqueous suspension, cream, lotion, gel, emulsion, drop, emulsion in hard or soft gel capsule, elixir, lyophilized cell powder and cell spray, or any combinations thereof.

16. The method of claim 14, wherein said conditioned medium comprises cytokine factors selected from the group comprising VEGF, Ang1, and TGFβ, or any combinations thereof; and wherein the conditioned medium induces neovascularization at the administered site.

* * * * *